(12) United States Patent
Hirai et al.

(10) Patent No.: US 11,648,168 B2
(45) Date of Patent: May 16, 2023

(54) MOVING IMAGE RECORDING SYSTEM

(71) Applicant: PARAMOUNT BED CO., LTD., Tokyo (JP)

(72) Inventors: Eita Hirai, Tokyo (JP); Kazuki Kouke, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 608 days.

(21) Appl. No.: 16/620,710

(22) PCT Filed: Oct. 9, 2018

(86) PCT No.: PCT/JP2018/037544
§ 371 (c)(1),
(2) Date: Dec. 9, 2019

(87) PCT Pub. No.: WO2019/082635
PCT Pub. Date: May 2, 2019

(65) Prior Publication Data
US 2021/0137762 A1    May 13, 2021

(30) Foreign Application Priority Data

Oct. 27, 2017    (JP) .............................. JP2017-208304

(51) Int. Cl.
*A61H 1/00*    (2006.01)
*G06V 40/20*    (2022.01)
(Continued)

(52) U.S. Cl.
CPC .............. *A61H 1/00* (2013.01); *G06V 40/23* (2022.01); *H04N 23/61* (2023.01); *A61H 2201/5043* (2013.01); *A61H 2201/5092* (2013.01)

(58) Field of Classification Search
None
See application file for complete search history.

(56) References Cited

U.S. PATENT DOCUMENTS 9,053,627 B2 * 6/2015 Yeh ........................... H04Q 9/00
9,411,457 B2 * 8/2016 Perlin ...................... G06F 3/045
(Continued)

FOREIGN PATENT DOCUMENTS

JP    2004-310350 A    11/2004
JP    2006-260082 A    9/2006
JP    2016-197330 A    11/2016

*Primary Examiner* — Talha M Nawaz
(74) *Attorney, Agent, or Firm* — Birch, Stewart, Kolasch & Birch, LLP

(57) ABSTRACT

A moving image recording system includes an information processor and a station to and from which the information processor is attachable and detachable. The station includes: a connection unit configured to be connected to the information processor and transmit and receive data to and from the information processor; an acquisition unit configured to acquire subject identification information for identifying a subject of an image; and a control unit configured to send the subject identification information, acquired by the acquisition unit, to the information processor via the connection unit. The information processor includes: a connection unit configured to be connected to the station and transmit and receive data to and from the station; an imaging unit configured to take an image of the subject; a storage unit configured to store a moving image taken by the imaging unit; and a recording controller configured to receive the subject identification information from the station via the connection unit, and write the moving image of the subject, taken by the imaging unit, into the storage unit while associating the moving image with the subject identification information thus received.

18 Claims, 23 Drawing Sheets

(51) Int. Cl.
*H04N 5/77* (2006.01)
*H04N 23/61* (2023.01)

(56) References Cited

U.S. PATENT DOCUMENTS

| | | | | |
|---|---|---|---|---|
| 10,070,805 | B1* | 9/2018 | Friedman | G08B 21/04 |
| 2008/0119763 | A1* | 5/2008 | Wiener | A61B 5/224 |
| | | | | 600/587 |
| 2012/0077163 | A1* | 3/2012 | Sucar Succar | A63B 23/16 |
| | | | | 434/247 |
| 2017/0000386 | A1* | 1/2017 | Salamatian | G16H 10/60 |
| 2017/0188864 | A1* | 7/2017 | Drury | A61B 5/02427 |
| 2017/0206691 | A1* | 7/2017 | Harrises | G02B 27/0172 |
| 2018/0228407 | A1* | 8/2018 | Olds | A61B 5/225 |
| 2019/0147721 | A1* | 5/2019 | Avitan | G06F 1/3209 |
| | | | | 340/573.1 |
| 2019/0371028 | A1* | 12/2019 | Harrises | G02B 27/0101 |

* cited by examiner

| SUBJECT | ACTION CATEGORY | DATE AND TIME | MOVING IMAGE |
|---|---|---|---|
| 0010 | STANDING UP | 2017/06/30 09:21 | 00000001 |
| 0010 | STANDING UP | 2017/06/30 09:22 | 00000002 |
| 0010 | STANDING UP | 2017/06/30 09:23 | 00000003 |
| 0010 | STANDING UP | 2017/06/30 13:43 | 00000004 |
| 0010 | STANDING UP | 2017/06/25 10:01 | 00000005 |
| 0010 | STANDING UP | 2017/06/25 14:32 | 00000006 |
| ... | ... | ... | ... |

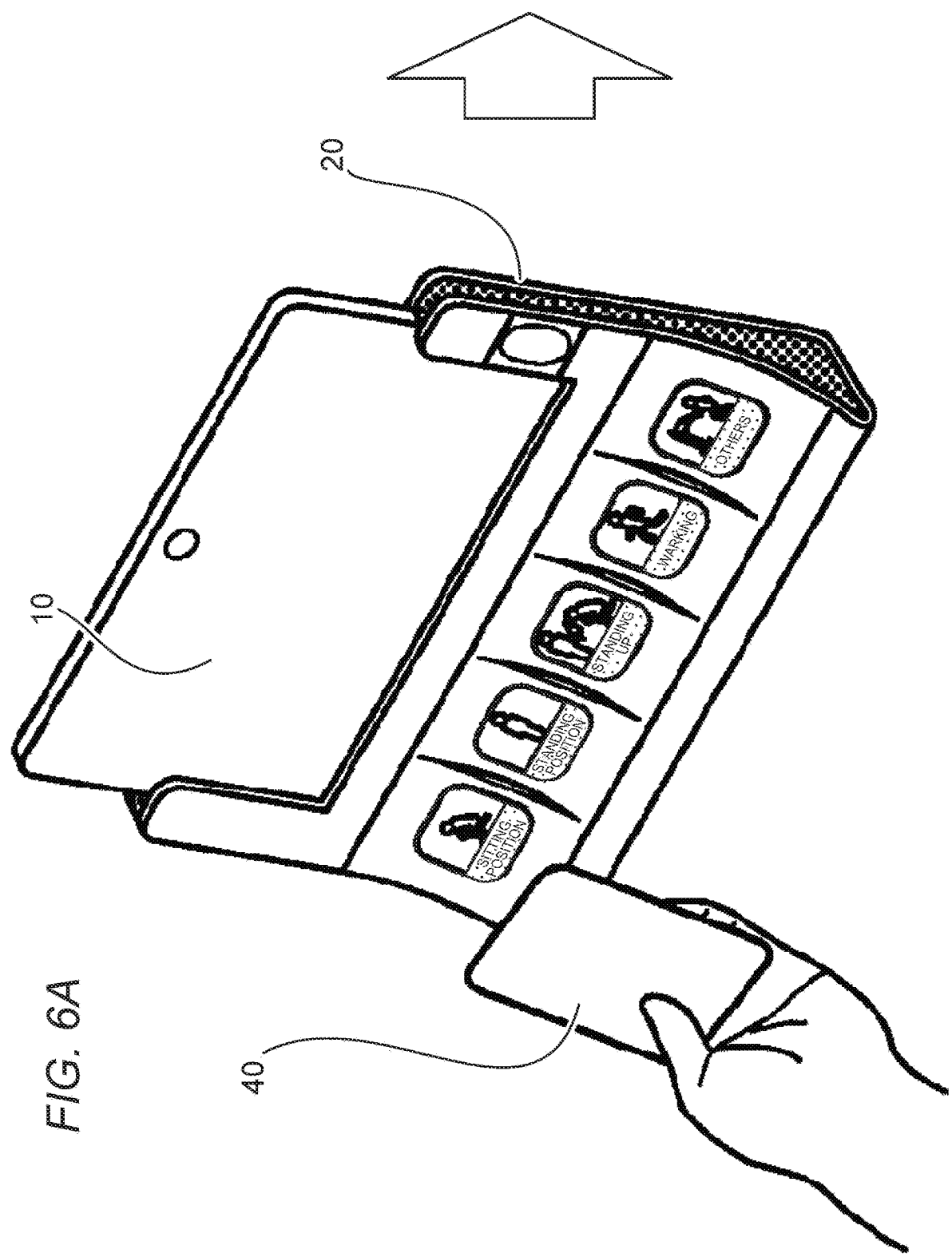

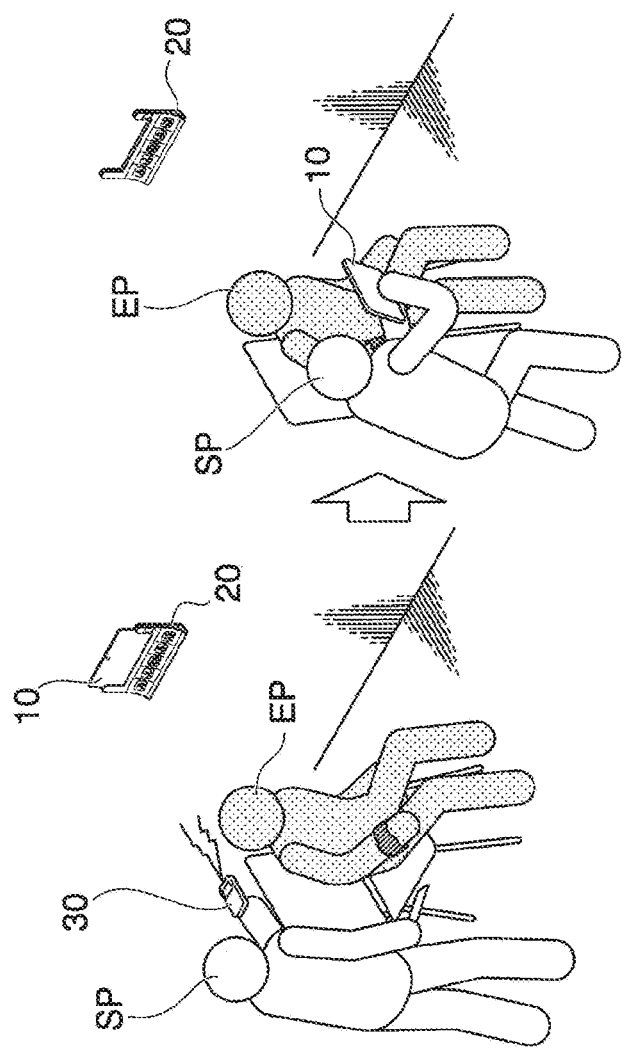

| SUBJECT | APPLICATION NAME | DATE AND TIME | MOVING IMAGE | RESULTANT IMAGE |
|---|---|---|---|---|
| 0010 | REACH PRACTICE | 2017/06/30 09:21 | M0000011 | R0000011 |
| 0010 | REACH PRACTICE | 2017/06/30 09:22 | M0000012 | R0000012 |
| 0010 | REACH PRACTICE | 2017/06/30 09:23 | M0000013 | R0000013 |
| 0010 | REACH PRACTICE | 2017/06/30 13:43 | M0000014 | R0000014 |
| 0010 | REACH PRACTICE | 2017/06/25 10:01 | M0000015 | R0000015 |
| 0010 | REACH PRACTICE | 2017/06/25 14:32 | M0000016 | R0000016 |
| ... | ... | ... | ... | ... | form
MOVING IMAGE RECORDING SYSTEM

TECHNICAL FIELD

The present invention relates to a moving image recording system.

This application claims priority based on Japanese Patent Application No. 2017-208304 filed in Japan on Oct. 27, 2017, the contents of which are incorporated herein by reference.

BACKGROUND ART

In the field of rehabilitation, people record moving images of a subject under rehabilitation and make use of these moving images for rehabilitation (for example, see PTL 1).

CITATION LIST

Patent Literature

PTL 1: Japanese Patent Application Publication No. 2016-197330

SUMMARY OF INVENTION

Technical Problem

The present invention aims to provide a moving image recording system which makes it possible to improve operability in a moving image recording system that takes images of a subject.

Solution to Problem

An aspect of the present invention is a moving image recording system including an information processor and a station to and from which the information processor is attachable and detachable, in which the station includes: a connection unit configured to be connected to the information processor and transmit and receive data to and from the information processor; an acquisition unit configured to acquire subject identification information for identifying a subject of an image; and a control unit configured to send the subject identification information, acquired by the acquisition unit, to the information processor via the connection unit, and the information processor includes: a connection unit configured to be connected to the station and transmit and receive data to and from the station; an imaging unit configured to take an image of the subject; a storage unit configured to store a moving image taken by the imaging unit; and a recording controller configured to receive the subject identification information from the station via the connection unit, and write the moving image of the subject, taken by the imaging unit, into the storage unit while associating the moving image with the subject identification information thus received.

Advantageous Effects of Invention

According to the present invention, it is possible to improve operability in a moving image recording system that takes images of a subject.

BRIEF DESCRIPTION OF DRAWINGS

FIGS. 6A to 6C are conceptual views illustrating a processing example in the rehabilitation support system in the first embodiment of the present invention.

DESCRIPTION OF EMBODIMENTS

Hereinbelow, embodiments of the present invention are described with reference to the drawings.

First Embodiment

Figure 1:
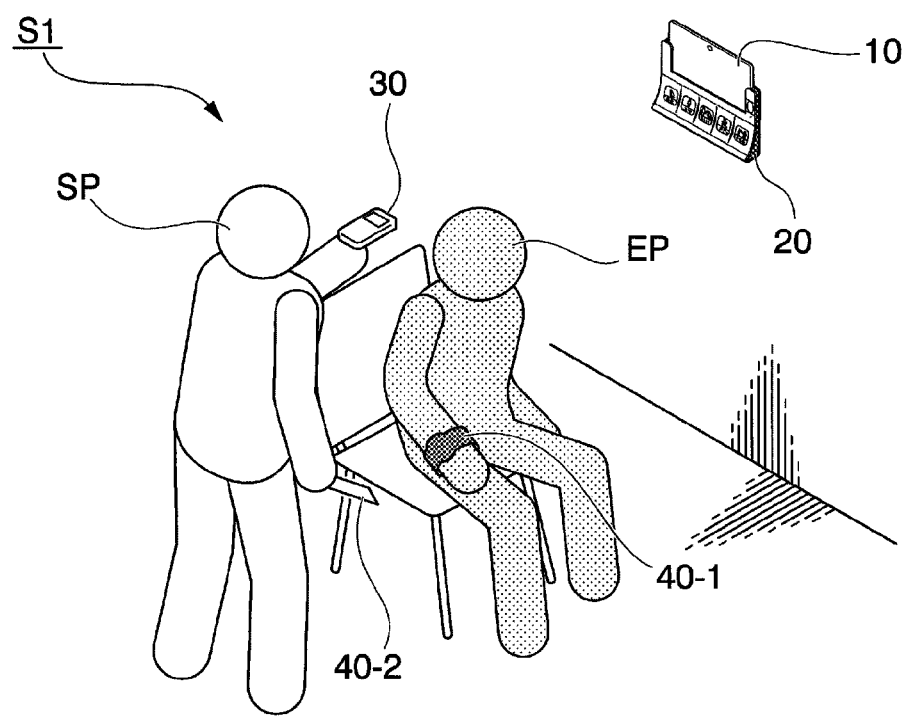
FIG. 1 is a perspective view illustrating the system configuration of a rehabilitation support system in a first embodiment of the present invention.

First, a first embodiment is described. FIG. 1 is a perspective view illustrating the system configuration of a rehabilitation support system S1 (moving image recording system) in this embodiment. The rehabilitation support system S1 is a system that provides support for rehabilitation on a subject to undergo rehabilitation EP (hereinafter referred to as a "subject EP"). More specifically, the rehabilitation support system S1 is a system for taking and recording moving images of how the subject EP undergoes rehabilitation, and reproducing and displaying the recorded moving images.

The rehabilitation support system S1 includes: a tablet terminal 10; a station 20; a remote controller 30, and devices 40-1, 40-2. In the following description, the devices 40-1, 40-2 are collectively referred to as devices 40 unless they need to be particularly distinguished from each other.

The tablet terminal 10 is a portable tablet type information processor. The tablet terminal 10 is attachable to the station 20 and detachable from the station 20.

The station 20 is a stationary station that can be installed on a wall of a room, for example. The tablet terminal 10 is attachable to and detachable from the station 20. When the tablet terminal 10 is attached, the station 20 keeps the tablet terminal 10 in a standing position with its front face facing the front. In addition, when the tablet terminal 10 is attached, the station 20 is connected to the tablet terminal 10 to transmit and receive data. The station 20 is connected to a power supply, and supplies power to the tablet terminal 10 automatically once the tablet terminal 10 is attached.

The remote controller 30 is a remote controller for manipulating the tablet terminal 10 by remote control. Buttons are arranged on a front face of the remote controller 30. The remote controller 30 is palm-size and has an easy-to-grasp design, for example.

The devices 40 are devices having an RFID (Radio Frequency Identifier) tag storing therein personal information of an owner. The personal information at least includes identification information for identifying the owner. The identification information of the subject EP is a patient number (subject identification information). In the illustrated example, the subject EP wears the band-type device 40-1 on his/her wrist. On the other hand, a helper SP, such as a physical therapist and an occupational therapist, that helps the rehabilitation of the subject EP (hereinafter referred to as a "helper SP") holds the card-type device 40-2 in his/her hand.

By making the device 40 in the shape of a band, the subject can always wear the device 40, thus making it possible to prevent the subject from forgetting to bring the device or losing the device. Note that, the devices 40 are not limited to an RFID and may be other noncontact IDs. In addition, the system may have such a configuration that the subject EP uses the card-type device 40-2 and the manipulator SP uses the band-type device 40-1; alternatively, the system may have such a configuration that both the subject EP and the helper SP use the band-type device 40-1 or both the subject EP and the helper SP use the card-type device 40-2. Further, the devices 40 do not necessarily have to be in the shape of a band or a card, and may have other shapes easy for the subject EP and the manipulator SP to hold or wear.

Figure 2:
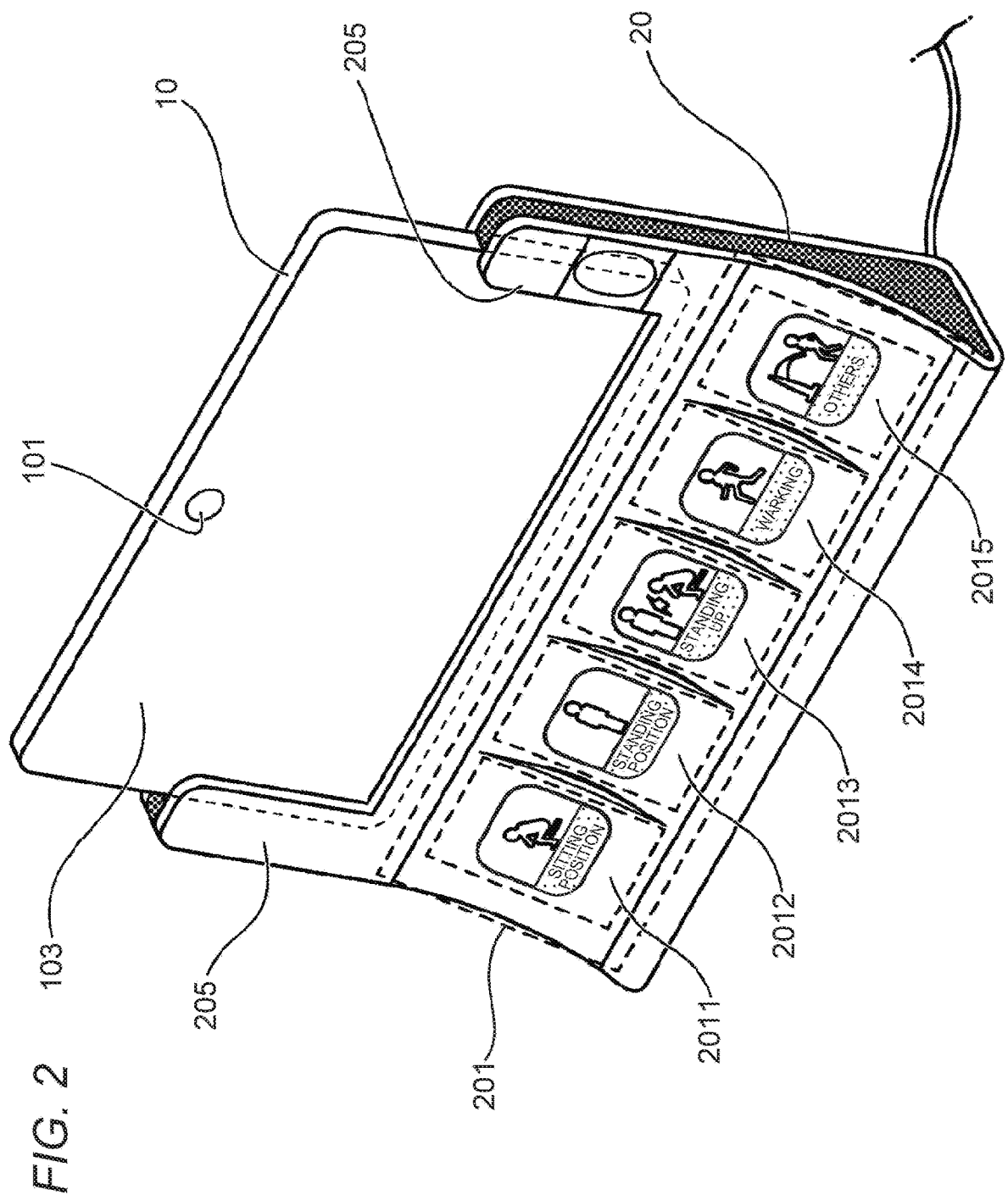
FIG. 2 is a perspective view illustrating an appearance example of a tablet terminal and a station equipped in the rehabilitation support system in the first embodiment of the present invention.

Next, a description is given of a configuration example of each of the tablet terminal 10, the station 20, the remote controller 30, and the device 40. FIG. 2 is a perspective view illustrating an appearance example of the tablet terminal 10 and the station 20 equipped in the rehabilitation support system S1.

The tablet terminal 10 includes an imaging unit 101 and a display unit 103 on its front face. The imaging unit 101 is a camera configured to take an image of a subject. For example, the imaging unit 101 takes an image of the subject EP undergoing rehabilitation. The display unit 103 is an image display device such as a liquid crystal display and an organic EL (Electro Luminescence) display. The display unit 103 includes a touch panel on its display screen. For example, the display unit 103 reproduces and displays a moving image stored in the tablet terminal 10.

The station 20 includes a pairing reader 201 on its front face. The pairing reader 201 is an acquisition unit configured to acquire personal information for identifying the subject EP and a rehabilitation-related action category. The pairing reader 201 reads personal information from the device 40. The pairing reader 201 is provided with five read areas 2011 to 2015. The read areas 2011 to 2015 are associated respectively with different action categories. The action categories indicate categories of actions during rehabilitation. In the illustrated example, the read area 2011 is associated with an action category "sitting position", the read area 2012 is associated with an action category "standing position", the read area 2013 is associated with an action category "standing up", the read area 2014 is associated with an action category "walking", and the read area 2015 is associated with an action category "others". The pairing reader 201 acquires an action category through the read areas 2011 to 2015 included in the personal information read from the device 40.

Note that the action categories are not limited to those described above, and a change or addition can be made thereto freely by settings. In addition, the action categories are not limited only to "actions" and may include categories such as ones indicating "tasks" and "exercise". Further, the system may have such a configuration that the read areas 2011 to 2015 are united into one and used exclusively for reading personal information, and that the action category is selected in an application equipped in the tablet terminal 10. Thereby, it is possible to update categories flexibly by updating an application.

The station 20 also has a docking unit 205. The docking unit 205 has a concave holder on its side faces, and holds the tablet terminal 10 by clipping side faces of the tablet terminal with this holder. The docking unit 205 may be movable right and left. Thereby, even in the case of holding the tablet terminal with its orientation changed from horizontal to vertical and changing the size of the tablet terminal 10, it is possible to fit the station 20 to the tablet terminal without changing the station.

Figure 3:
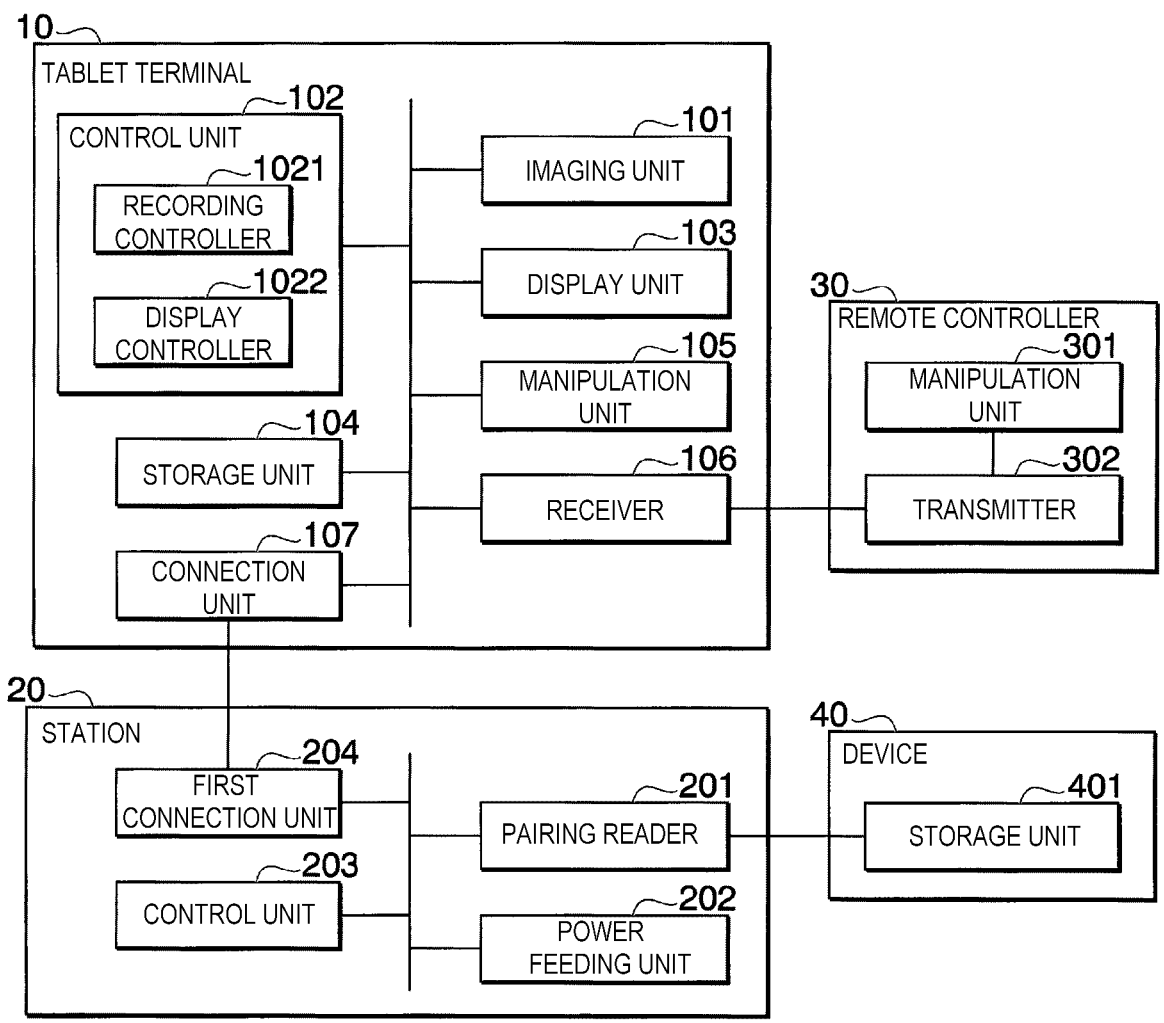
FIG. 3 is a schematic block diagram illustrating a functional configuration example of each of the tablet terminal, the station, a remote controller, and media equipped in the rehabilitation support system in the first embodiment of the present invention.

FIG. 3 is a schematic block diagram illustrating a functional configuration example of each of the tablet terminal 10, the station 20, the remote controller 30, and the device 40 equipped in the rehabilitation support system S1.

The tablet terminal 10 includes: the imaging unit 101; a control unit 102; the display unit 103; a storage unit 104; a manipulation unit 105; a receiver 106; and a connection unit 107. Note that, the system may have such a configuration that the tablet terminal 10 has no imaging unit 101, and acquires a moving image, taken by an external camera, through the connection unit 107 and uses the image thus acquired. More specifically, for example, the system may have such a configuration that an external camera (such as a web camera) which is separate from the tablet terminal 10 is disposed, and an image is taken by this external camera instead of the imaging unit 101. In this case, the external camera may send a taken moving image to the tablet terminal 10 in real time, or may save the moving image therein temporarily without sending them. In the case of temporarily save a taken moving image in the external camera, the external camera may send the moving image to the tablet terminal 10 upon receipt of instructions from the tablet terminal 10.

The control unit 102 is constituted of a CPU (Central Processing Unit), and configured to control the overall operations of the tablet terminal 10. The control unit 102 includes: a recording controller 1021; and a display controller 1022. The recording controller 1021 is configured to record a moving image of the subject EP taken by the imaging unit 101, and write and save the recorded moving image in the storage unit 104 while associating it with the patient number of the subject EP and his/her rehabilitation-related action category, which are received from the station 20, and the time and date when the moving image is taken. The display controller 1022 is configured to reproduce and display the moving image, which is stored in the storage unit 104, on the display unit 103. The display controller 1022 is also configured to reproduce multiple (e.g. two) moving images of the subject EP at the same time while displaying them on the display unit 103 side by side.

The storage unit 104 is constituted of a storage device such as a ROM (Read Only Memory) and a RAM (Random Access Memory), and configured to store various kinds of information. For example, the storage unit 104 stores data such as image data of a moving image taken by the imaging unit 101 (hereinafter referred to as moving image data) and a correspondence table in which the moving image, the subject, the action category, and the time and date when the image is taken are associated with each other.

The manipulation unit 105 is constituted of an existing input device such as a button and a touch panel, and configured to accept inputs. The manipulation unit 105 is manipulated by the helper SP when the helper SP inputs his/her instructions into the tablet terminal 10.

The receiver 106 is configured to receive control data from the remote controller 30 via infrared light, for example. The control data includes start information that instructs start of recording a moving image and stop information that instructs stop of recording a moving image.

The connection unit 107 is an interface that is configured to be connected to the station 20 and transmit and receive data to and from the station when the tablet terminal 10 is attached to the station 20.

Note that, the tablet terminal 10 may have a function unit, such as an audio output unit that outputs audio, that smartphones and tablet terminals typically have.

The station 20 includes: the pairing reader 201; a power feeding unit 202; a control unit 203; and a first connection unit 204.

The power feeding unit 202 is configured to feed power to each unit of the station 20. The power feeding unit 202 is also configured to feed power to the tablet terminal 10 via the first connection unit 204 when the tablet terminal 10 is attached to the station 20.

The control unit 203 is configured to control the overall operations of the station 20. The control unit 203 may be constituted of a CPU. The control unit 203 sends data, such as personal information and an action category read from the device 40 by the pairing reader 201, to the tablet terminal 10 via the first connection unit 204. The first connection unit 204 is an interface that is configured to be connected to the tablet terminal 10 and transmit and receive data to and from the tablet terminal when the tablet terminal 10 is attached to the station 20.

Note that, a part of or the entire functions of the station 20 may be implemented by an application of the tablet terminal 10.

The remote controller 30 includes: a manipulation unit 301; and a transmitter 302. The manipulation unit 301 is constituted of a button and configured to accept inputs. The transmitter 302 is configured to send control data to the tablet terminal 10 via infrared light, for example, when the manipulation unit 301 accept inputs.

The device 40 includes a storage unit 401. The storage unit 401 is configured to store personal information of an owner. The personal information includes a patient number, a name, and a date of birth, for example.

Figures 4, 5:
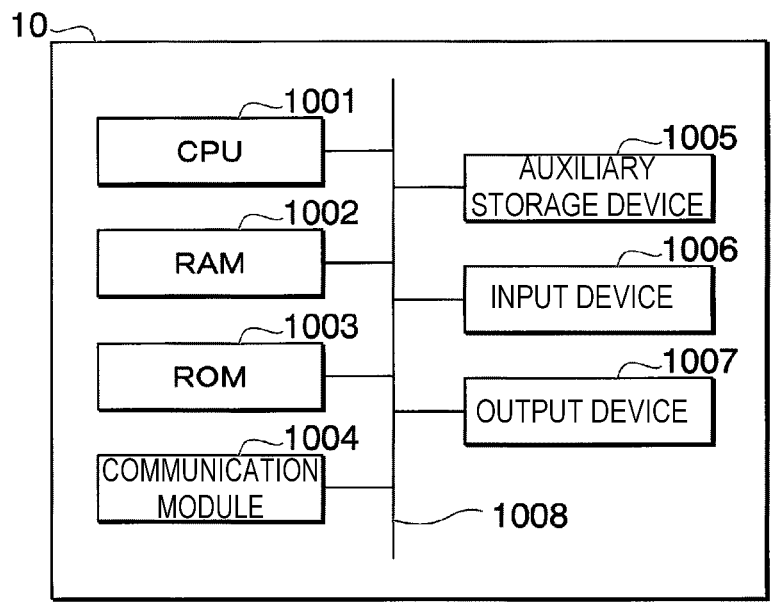
FIG. 4 is a schematic block diagram illustrating a hardware configuration example of the tablet terminal in the first embodiment of the present invention.
FIG. 5 is a schematic diagram illustrating the data configuration and a data example of a correspondence table stored in a storage unit of the tablet terminal in the first embodiment of the present invention.

FIG. 4 is a schematic block diagram illustrating a hardware configuration example of the tablet terminal 10 equipped in the rehabilitation support system S1.

The tablet terminal 10 is constituted of: a CPU 1001; a RAM 1002; a ROM 1003; a communication module 1004; an auxiliary storage device 1005; an input device 1006; and an output device 1007 which are connected to each other via a bus line 1008, for example.

The CPU 1001 corresponds to the control unit 102. The RAM 1002, the ROM 1003, and the auxiliary storage device 1005 correspond to the storage unit 104. The communication module 1004 corresponds to the receiver 106 and the connection unit 107. The input device 1006 corresponds to the imaging unit 101. The output device 1007 corresponds to the display unit 103.

FIG. 5 is a schematic diagram illustrating the data configuration and a data example of a correspondence table stored in the storage unit 104 of the tablet terminal 10. As illustrated in the drawing, the correspondence table has fields of: a subject; an action category, time and date; and a moving image. The subject indicates a patient number of the subject EP who is a moving image target. The action category indicates a rehabilitation action category. The time and date indicates the year, month, day, hour, and minute when the moving image is taken. The moving image indicates a data name of moving image data.

Figure 7:
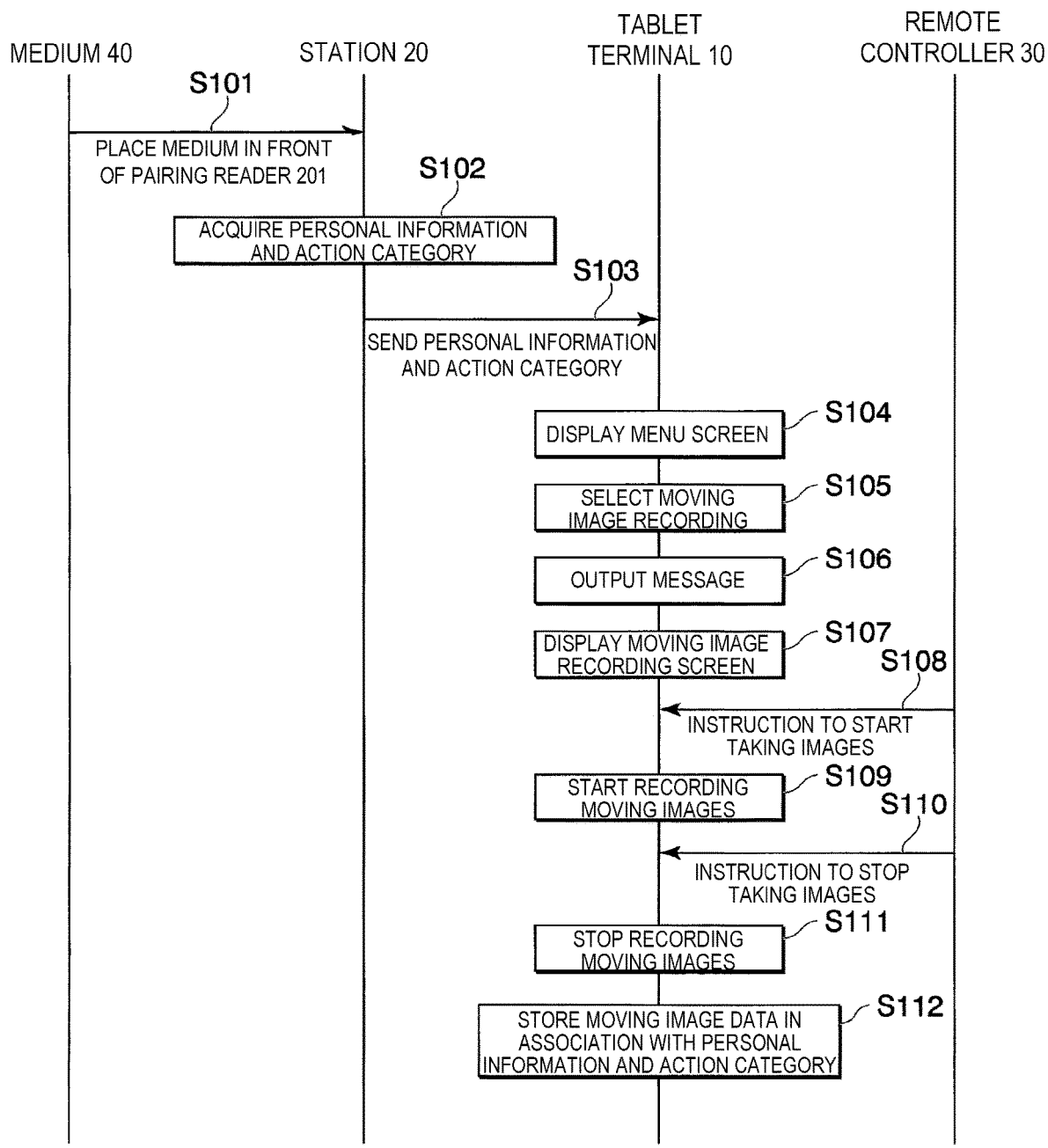
FIG. 7 is a sequence diagram illustrating the processing example in the rehabilitation support system in the first embodiment of the present invention.

Next, with reference to FIGS. 6 and 7, a description is given of the flow of processing in the rehabilitation support system S1 in this embodiment. FIGS. 6A to 6C are conceptual views illustrating a processing example in the rehabilitation support system S1. FIG. 7 is a sequence diagram illustrating the processing example in the rehabilitation support system S1. In the rehabilitation support system S1, it is possible to record how the subject EP undergoes rehabilitation in the form of a moving image using the tablet terminal 10, and reproduce and check the recorded moving image in the tablet terminal 10.

The tablet terminal 10 is previously attached to the station 20 installed on a wall, for example. This makes it possible to save the helper SP the trouble of setting a tripod and a camera for taking a moving image while adjusting the position of the tripod, the height of the camera, and the like so that the camera can capture the subject EP. In addition, conducting fixed-point observation at the previous setting point by setting the position of a camera using a tripod and the like requires a lot of work or sometimes causes positional misalignment. On the other hand, in this rehabilitation support system S1, easy setting is possible by only attaching the tablet terminal 10 to the station 20. In addition, since the position of the tablet terminal 10 is never misaligned from the previous position, it is possible to take rehabilitation moving images in the same range every time only by determining the position of the subject EP in advance, and thus easily perform comparison between moving images, for example. Further, since the station 20 is installed on a wall face or the like, it does not ordinarily get in the way in a rehabilitation room where various people come and go and does not need to be cleared up, and can be used immediately when needed.

First, the helper SP places the device 40, corresponding to the subject EP, in front of the pairing reader 201 of the station 20 (Step S101) (see FIG. 6A). At this time, the helper SP places the device 40 in front of the read area of the pairing reader 201 corresponding to the action category that the subject EP is going to do (i.e. the action category to be recorded in the form of a moving image). In the illustrated example, the device 40 is placed in front of the read area 2011 corresponding to the action category "sitting position".

The pairing reader 201 of the station 20 reads personal information of the subject EP from the device 40, and acquires the action category corresponding to the read area over which the device 40 is placed (Step S102). Then, the pairing reader 201 outputs the acquired personal information and action category to the control unit 203. The control unit 203 sends the input personal information and action category to the tablet terminal 10 via the first connection unit 204 (Step S103).

Upon receipt of the personal information and the action category from the station 20, the control unit 102 of the tablet terminal 10 displays, on the display unit 103, a menu screen according to the personal information thus received (Step S104). On the menu screen, various menus such as: patient card registration for registering the personal information of the subject EP into the device 40; various settings; moving image reproduction for reproducing moving images; moving image transfer for transferring moving images to another equipment; moving image recording for recording moving images; and logout are selectively displayed. The helper SP selects moving image recording from the menu screen (Step S105).

Upon selection of moving image recording on the menu screen (Step S105), the control unit 102 calculates recordable time out of a free space for moving image recording in the storage unit 104 and displays the calculated time on the display unit 103 (Step S106). For example, the control unit 102 displays a message like "another xx MB (approx. yy minutes) recordable" on the display unit 103.

Then, the control unit 102 initiates the imaging unit 101, and displays a moving image recording screen for moving image recording on the display unit 103 (Step S107). An image taken by the imaging unit 101 is displayed on the moving image recording screen. Since the screen of the display unit 103 of the tablet terminal 10 is disposed on the same face as the imaging unit 101, the imaging unit can take an image in a state where the helper SP and the subject EP can see the screen of the display unit 103. By displaying an image, taken by the imaging unit 101, on the moving image recording screen, the helper SP can check how the subject EP looks in a picture before starting moving image recording or during recording. In addition, the received personal information and action category are displayed on the moving image recording screen. This makes it possible to reduce a mistake in registration of moving images.

After the moving image recording screen is displayed on the tablet terminal 10, the helper SP presses a button, located in the manipulation unit 301 of the remote controller 30, to give instructions to start recording (Step S108) (see FIG. 6B). Once the manipulation unit 301 accepts an input, the transmitter 302 of the remote controller 30 sends start information to the tablet terminal 10. Once the receiver 106 of the tablet terminal 10 receives the start information, the recording controller 1021 of the control unit 102 of the tablet terminal 10 starts recording of a moving image taken by the imaging unit 101 (Step S109). Note that, the helper may start recording of a moving image by pressing a start button displayed on the tablet terminal 10 instead of using the remote controller 30.

Then, when the subject EP finishes the rehabilitation action, the helper SP presses the button, located in the manipulation unit 301 of the remote controller 30, again to give instructions to stop recording (Step S110). In this way, since the helper SP can manipulate the tablet terminal 10 using the remote controller 30, the helper can take a moving image at a location away from the tablet terminal 10. This enables the helper to stay close to the subject EP during rehabilitation and perform rehabilitation safely. In addition, by arranging only a minimum number (e.g. one) of buttons in the manipulation unit 301 of the remote controller 30, a reduction in manipulation error and sensory manipulation are possible. Note that, the helper may stop recording of a moving image by pressing a stop button displayed on the tablet terminal 10 instead of using the remote controller 30.

As described above, Steps S108 and S110 above may be performed using the tablet terminal 10 instead of the remote controller 30. In this case, in Step S108, the helper SP manipulates the tablet terminal 10 to start recording after the moving image recording screen is displayed on the tablet terminal 10. In addition, in Step S110, when the subject EP finishes the rehabilitation action, the helper SP manipulates the tablet terminal 10 again to stop recording.

Here, in this case, the system may be configured to save a moving image temporarily stored in the tablet terminal 10 after the moving image is edited to change its start point and end point. In this case, it is possible to achieve a moving image within a necessary time range without using the remote controller 30. On the other hand, the mode of using the remote controller 30 is advantageous in that no editing work is required and thus manipulation is easy.

Once the manipulation unit 301 accepts an input, the transmitter 302 of the remote controller 30 sends stop information to the tablet terminal 10. Once the receiver 106 receives the stop information, the recording controller 1021 of the control unit 102 of the tablet terminal 10 stops recording of a moving image taken by the imaging unit 101 (Step S111), and writes and saves moving image data in the storage unit 104 (Step S112). At this time, the recording controller 1021 of the control unit 102 stores the moving image in association with the patient number included in the personal information and the action category, which are received from the station 20, and the time and date when the moving image recording ends (the time and date when the image is taken). Specifically, the recording controller 1021 of the control unit 102 writes the patient number, the action category, the time and date when the image is taken, and the moving image in the correspondence table stored in the storage unit 104 while associating them with each other.

In other words, the subject, the action category, and the time and date when the image is taken are associated with the moving image automatically with a simple action of placing the device 40 in front of the read area corresponding to the action category. This is because, since the read area is provided for every action category, it is possible to specify the action category simply by changing the location over which the device 40 is placed. To put it another way, with a single action of placing the device 40 in front of the read area, it is possible to input the personal information and the action category to be associated with the moving image. Thereby, it is possible to save the helper SP the trouble of entering these sets of information into the tablet terminal 10, and thus improve operability. This makes it possible to reduce the operational burden of the helper SP.

Further, the recorded moving image can be reproduced then and there. For example, the helper SP can detach the tablet terminal 10 from the station 20 and check the recorded moving image with the subject EP (see FIG. 6C). Since the screen of a video camera is typically smaller in size than the screen of the tablet terminal 10, the subject EP whose eyes are getting worse, such as an elderly person, finds it difficult to check a moving image in the screen of a video camera. On the other hand, in this rehabilitation support system S1, since the recorded moving image can be reproduced in a relatively large screen of the tablet terminal 10, the helper can let the subject EP see and check the moving image at the location where the image is taken. Alternatively, the recorded moving image may be transferred to and displayed on another display device connected by wire or wireless to the tablet terminal 10. Thereby, it is possible to check the moving image in a larger screen or multiple screens.

In addition, since the tablet terminal 10 is detachable from the station 20, the subject EP does not need to go to the location where the station 20 is placed. Because the location of the subject EP is the point of taking an image, it is often located away from the station 20. In this case, the helper can detach the tablet terminal 10 from the station 20 and brings it to the place of the subject EP. Thereby, the helper SP and the subject EP can check and share the recorded moving image at the location where the image is taken. Further, while checking the recorded moving image, the helper SP and the subject EP may touch the moving image, write a handwritten drawing (marker) and a handwritten memo onto the image, and save these marker and memo together with the moving image. In this case, the helper SP and the subject EP can share the information more easily.

Once the moving image recording is over, the display controller 1022 of the control unit 102 of the tablet terminal displays, on the display unit 103, a moving image reproduction screen for reproducing the recorded moving image.

Figure 8:
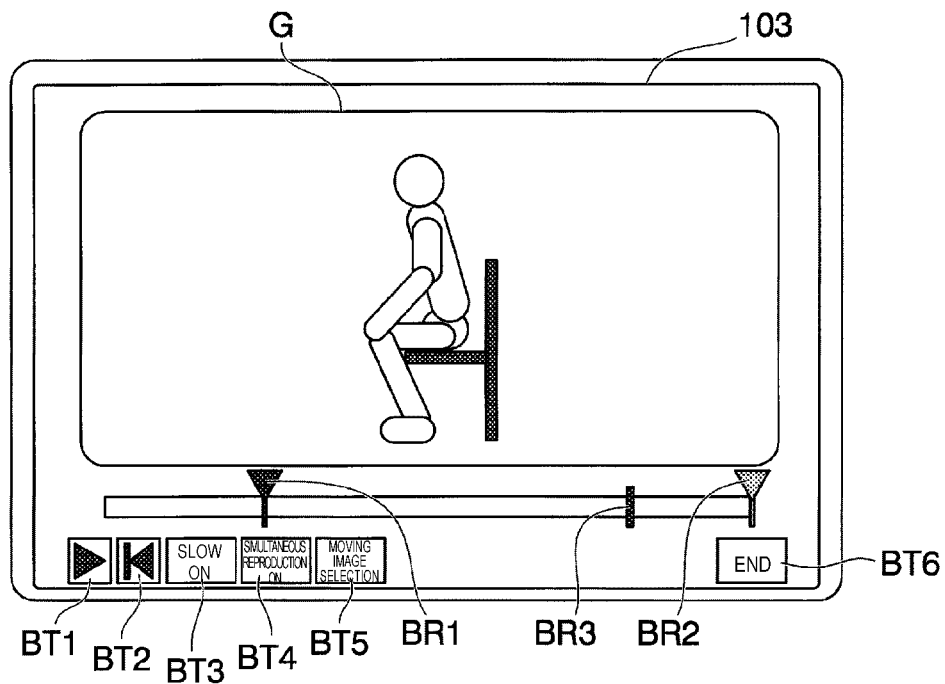
FIG. 8 is a conceptual view illustrating an example of a moving image reproduction screen displayed on a display unit of the tablet terminal in the first embodiment of the present invention.

FIG. 8 is a conceptual view illustrating an example of a moving image reproduction screen displayed on the display unit 103 of the tablet terminal 10. In the moving image reproduction screen illustrated in this drawing, a reproduction area G for reproducing a moving image, a reproduction button BT1 for reproducing a moving image, a reset button BT2 for resetting the current reproduction position to a reproduction start position, a slow ON button BT3 for reproducing a moving image at a slow rate, a simultaneous reproduction ON button BT4 for reproducing multiple moving images at the same time, a moving image selection button BT5 for selecting a moving image to be reproduced, and an end button BT6 for ending the moving image reproduction screen and moving back to the original screen are arranged.

Once the reproduction button BT1 is pressed in the moving image reproduction screen and its input is accepted, the display controller 1022 of the control unit 102 reproduces a moving image in the reproduction area G. Meanwhile, once the reset button BT2 is pressed in the moving image reproduction screen and its input is accepted, the display controller 1022 of the control unit 102 reproduces the moving image in the reproduction area G from the start. Meanwhile, once the slow ON button BT3 is pressed in the moving image reproduction screen and its input is accepted, the display controller 1022 of the control unit 102 slows down the rate of reproduction of the moving image in the reproduction area G. By reproducing the moving image at a slow rate, it is possible to easily analyze or comprehend a quick action such as a standing up action. In particular, in the case of checking the moving image with the subject EP, a slow-rate reproduction is easier to understand for a person such as an elderly person. Meanwhile, once the moving image selection button BT5 is pressed in the moving image reproduction screen and its input is accepted, the display controller 1022 of the control unit 102 displays, on the display unit 103, the moving image selection screen for selecting a moving image to be reproduced in the moving image reproduction screen. Meanwhile, once the end button BT6 is pressed in the moving image reproduction screen and its input is accepted, the display controller 1022 of the control unit 102 ends the moving image reproduction screen and displays the menu screen on the display unit 103.

Further, in the moving image reproduction screen, a reproduction location bar BR1, an end location bar BR2, and a current position bar BR3 are arranged below the reproduction area G. The reproduction location bar BR1 is a bar for adjusting the position to start reproduction. The end location bar BR2 is a bar for adjusting the position to end reproduction. The current position bar BR3 is a bar for indicating the current reproduction position. The position of each of the reproduction location bar BR1 and the end location bar BR2 can be changed by manipulation on the touch panel, for example.

In other words, the helper SP can adjust the moving image reproduction location. For example, the helper SP presses the reproduction button BT1 after adjusting the position of each of the reproduction location bar BR1 and the end location bar BR2. The display controller 1022 of the control unit 102 of the tablet terminal 10 reproduces a moving image in the reproduction area G from a location corresponding to the reproduction location bar BR1 and stops reproduction of the moving image at a location corresponding to the end location bar BR2. To put it another way, the moving image is reproduced from the position of the reproduction location bar BR1 to the position of the end location bar BR2. Thereby, only the part of action the helper and/or the subject wants to see can be pinpointed and reproduced. At the time of checking the moving image, the helper and/or the subject often reproduces it multiple times, and the first half of the moving image is an action preparation period and often meaningless, and thus changing the reproduction position is beneficial.

Further, the tablet terminal 10 can reproduce a moving image taken in the past and a moving image taken this time at the same time in order to compare the current action (the rehabilitation behavior) with the past action. First, the helper SP presses the simultaneous reproduction ON button BT4. Once the simultaneous reproduction ON button BT4 is pressed in the moving image reproduction screen and its input is accepted, the display controller 1022 of the control unit 102 of the tablet terminal 10 displays, on the display unit 103, the moving image selection screen for selecting the past moving image to be reproduced at the same time.

Figure 9A:
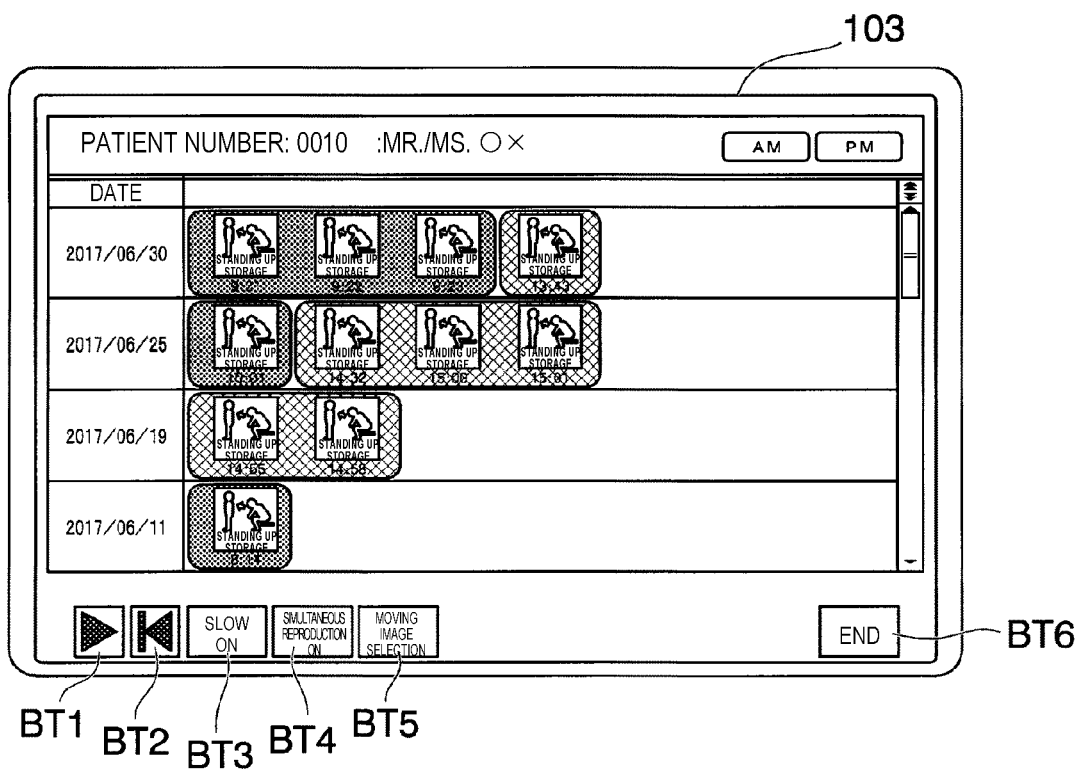
FIG. 9A is a conceptual view illustrating an example of a moving image selection screen displayed on the display unit of the tablet terminal in the first embodiment of the present invention.

FIG. 9A is a conceptual view illustrating an example of the moving image selection screen displayed on the display unit 103 of the tablet terminal 10. In the moving image selection screen illustrated in this drawing, the patient number and name of the subject EP are displayed in its upper left portion, and icons indicating moving images of the subject EP are selectively listed. Each icon is constituted of a pictogram and a text indicating the action category of the corresponding moving image. Thereby, the action category of the moving image can be identified easily. In addition, by representing the action category with a pictogram, it is possible to transmit the content of the action category intuitively without language constraint, thus implementing representation suitable for globalization.

As illustrated in the drawing, the icons are displayed while being sorted by date when the moving images are taken. In addition, the time when the image is taken is displayed below each icon. Further, each icon is displayed in such a manner that whether the time when the image is taken in the corresponding date is in the morning or in the afternoon is easily identifiable. For example, the icons can be separated by color in such a way that icons in the morning are circled with a red area while icons in the afternoon are circled with a blue area.

Note that, only moving images belonging to the action category of the moving image reproduced in the moving image reproduction screen (i.e. the action category corresponding to the read area included in the personal information read from the device 40 by the station 20) may be listed in the moving image selection screen. Alternatively, the icons may be displayed in the moving image selection screen while being sorted by action categories.

In the moving image selection screen, the helper SP selects and presses the icon of the moving image to be reproduced at the same time. The display controller 1022 of the control unit 102 of the tablet terminal 10 reads, from the storage unit 104, the moving image of the icon selected in the moving image selection screen, and displays a simultaneous reproduction screen on the display unit 103.

Figure 9B:
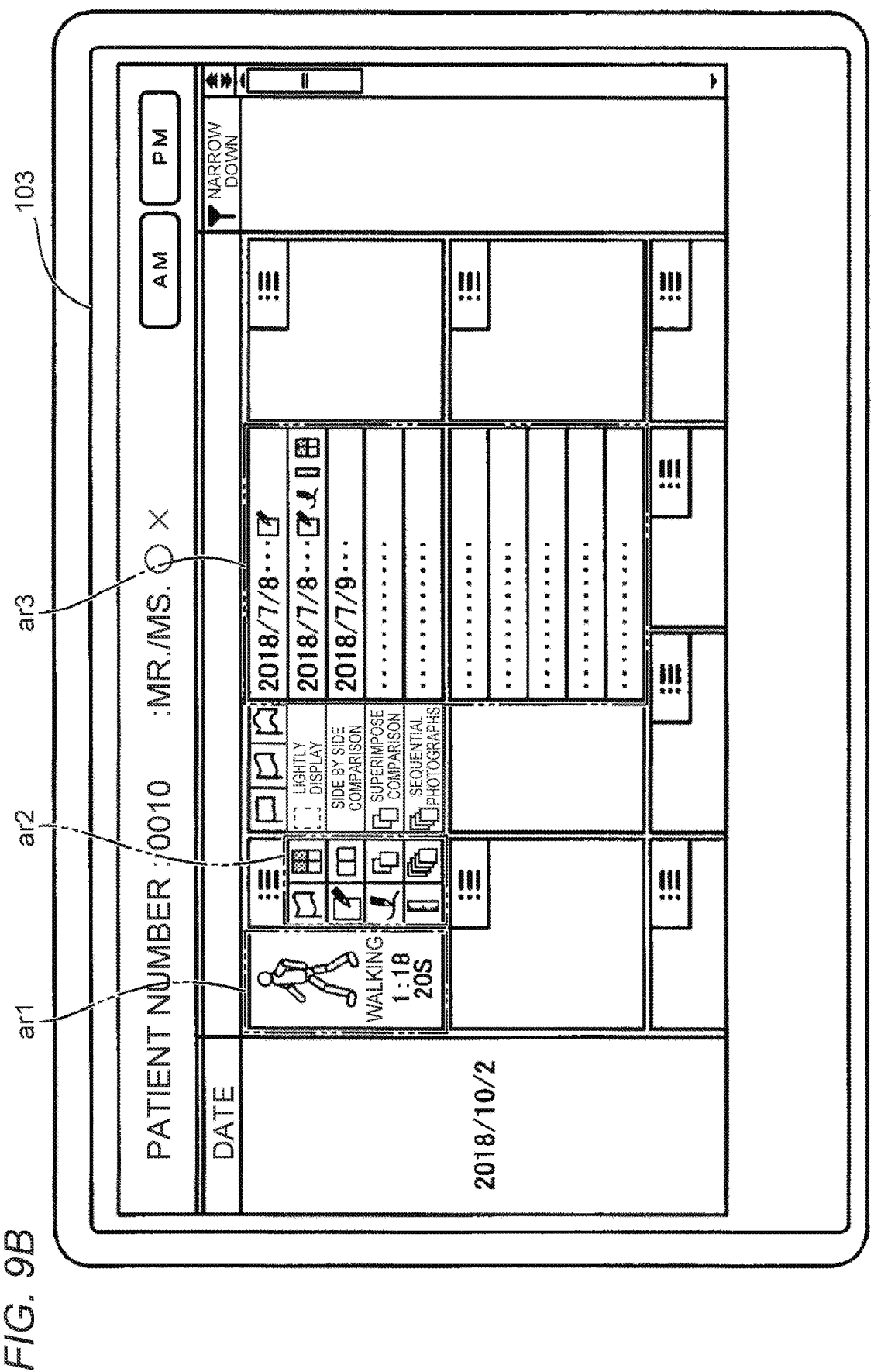
FIG. 9B is a conceptual view illustrating a modified example of the moving image selection screen.

As a modified example of the moving image selection screen illustrated in FIG. 9A, a moving image selection screen illustrated in FIG. 9B may be employed. In this modified example, the edit content of markers, memos, and the like appended to moving images can be checked through icons.

Figure 10:
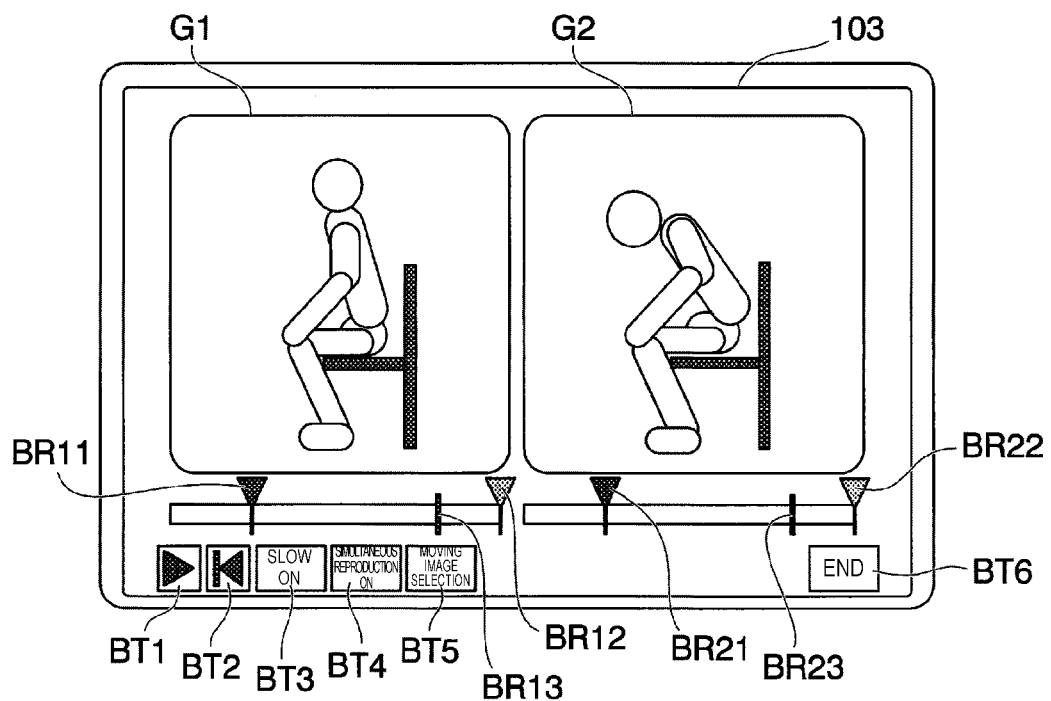
FIG. 10 is a conceptual view illustrating an example of a simultaneous reproduction screen displayed on the display unit of the tablet terminal in the first embodiment of the present invention.

In a region ar1 illustrated in FIG. 9B, the action category, the time and date the image is taken, and the moving image period are displayed. In addition, in a region ar2 illustrated in FIG. 9B, the following kinds of edit data linked to the moving image are illustrated by icons.
 flag: the importance level of data can be selected as needed
 written memo data exists
 freely drawn marker data exists
 various kinds of measurement data exist (for example, data on the angle of a raised arm and the tilt angle of a body trunk exist)
 photomosaic data exists
 sequential photographs creation data exists
 double-screen comparison data exists
 superimpose comparison data exists Further, in a region ar3 illustrated in FIG. 9B, the following kinds of edit data linked to each of the double-screen comparison data, the superimpose comparison data, and the sequential photographs data are illustrated by icons.
 written memo data exists
 freely drawn marker data exists
 various kinds of measurement data exist
 photomosaic data exists FIG. 10 is a conceptual view illustrating an example of the simultaneous reproduction screen displayed on the display unit 103 of the tablet terminal 10. In the simultaneous reproduction screen illustrated in this drawing, this time's reproduction area G1 for reproducing a moving image taken this time, a past reproduction area G2 for reproducing a moving image taken in the past, and the buttons BT1 to BT6 are arranged. This time's moving image is a moving image reproduced in the moving image reproduction screen, and is a moving image taken most recently, for example. In addition, the past moving image is a moving image selected in the moving image selection screen. The functions of the buttons BT1 to BT6 in the simultaneous reproduction screen are the same as those in the moving image reproduction screen.

Once the reproduction button BT1 is pressed in the simultaneous reproduction screen and its input is accepted, the display controller 1022 of the control unit 102 reproduces this time's moving image in the reproduction area G1 and the past moving image in the reproduction area G2 at the same time. In other words, the tablet terminal 10 can reproduce this time's moving image and the past moving image side by side at the same time. Since the tablet terminal can reproduce the two moving images side by side at the same time in one screen, it is possible to easily compare the current moving image with the past moving image at the location where the image is taken. Accordingly, the subject EP can easily check on site how much his/her condition has been recovered (rehabilitation effect) as compared with the past (e.g. when the subject entered the hospital). In addition, the helper SP and the subject EP can compare the moving images and share the problem at the location where the image is taken, and execute a rehabilitation menu to deal with the problem.

Note that, when the past and current moving images are displayed side by side for comparison, their positions may be changed, or their sizes may be increased or decreased.

In addition, the current moving image may be displayed side by side in two versions with different magnification ratio, e.g. one of the moving images is a bird's eye view image and the other is a moving image partially enlarging this bird's eye view image.

Further, two moving images of a moving image of a third party other than a patient, such as a therapist, and a moving image of the subject EP may be displayed side by side. In this case, the action of the subject EP may be compared with the action of the third party such as a therapist using the action of the third party as a good example.

Furthermore, when multiple moving images are arranged side by side and compared, they do not necessarily have to be arranged in a lateral direction and may be arranged in a longitudinal direction. When the moving images are arranged in the longitudinal direction, a reproduction location bar BR11, an end location bar BR12, and a current position bar BR13 to be described later may be arranged right beside the moving images longitudinally arranged, or may be arranged right below the moving images longitudinally arranged.

In the simultaneous reproduction screen, the reproduction location bar BR11, the end location bar BR12, and the current position bar BR13 corresponding to this time's moving image are arranged below this time's reproduction area G1. In the meantime, in the simultaneous reproduction screen, a reproduction location bar BR21, an end location bar BR22, and a current position bar BR23 corresponding to the past moving image are arranged below the past reproduction area G2. The helper SP can adjust the reproduction location of this time's moving image by changing the position of the reproduction location bar BR11 and the position of the end location bar BR12. In addition, the helper SP can adjust the reproduction location of the past moving image by changing the position of the reproduction location bar BR21 and the position of the end location bar BR22.

For example, a time period before an action starts from the start of moving image recording sometimes differs from one moving image to another. Accordingly, even when two moving images are reproduced at the same time, the subject EP does not always start the action in these moving images at the same time. For this reason, if the two moving images are reproduced directly from the start, they are hard to compare because the action timing of the subject EP differs from one moving image to another. To solve this problem, it is possible to adjust the reproduction location of each moving image to its action start timing, for example, so that the action timings of the subject EP in the two moving images match each other.

For example, the helper SP presses the reproduction button BT1 after adjusting the reproduction location bar BR11 and the reproduction location bar BR21 to their action start timing positions. The display controller 1022 of the control unit 102 of the tablet terminal 10 reproduces, at the same time, this time's moving image from the location corresponding to the reproduction location bar BR11 and the past moving image from the location corresponding to the reproduction location bar BR 21. Thereby, since the subject EP starts an action at the same time in the two moving images when these two moving images are reproduced at the same time, it is possible to compare their difference and easily check a change such as a change in action speed. The reproduction location bars BR1, BR11, and BR21 and the end location bars BR2, BR12, and BR22 constitute a reproduction position specification unit configured to specify a reproduction position of a moving image. The display controller 1022 reproduces a moving image at a reproduction position specified by the reproduction position specification unit.

In addition, the tablet terminal 10 can select and reproduce not only this time's moving image but also any desired moving image recorded. For example, once moving image reproduction is selected in the menu screen, the control unit 102 displays, on the display unit 103, a moving image selection screen for selecting a moving image to be reproduced. In this moving image selection screen, one or two moving images can be selected. If one moving image is selected in the moving image selection screen, the control unit 102 displays, on the display unit 103, a moving image reproduction screen for reproducing the selected moving image. On the other hand, if two moving images are selected in the moving image selection screen, the control unit 102 displays, on the display unit 103, a simultaneous reproduction screen for reproducing the selected two moving images at the same time.

Further, the tablet terminal 10 can perform data migration of transferring a recorded moving image to another equipment such as a personal computer or a cloud (server device). For example, once moving image transfer is selected in the menu screen, the control unit 102 displays a moving image selection screen for selecting a moving image to be transferred, and transfers data (moving image data and correspondence data associated with the moving image in the correspondence table (the subject, the action category, and the time and date)) on the moving image selected in the moving image selection screen. For example, the data may be transferred using a computer-readable recording medium, or using a wireless communication such as a wireless LAN (Local Area Network) and Bluetooth (registered trademark).

Note that, when the tablet terminal 10 performs data migration of transferring a recorded moving image to another equipment, data on memos and markers appended to the moving image may be migrated together with the moving image data.

In addition, the storage unit 104 cannot record anymore moving images if its free space is decreased; hence, in order to prevent this, the tablet terminal 10 may automatically perform data migration of transferring data on a moving image to another equipment. Thereby, capacity overload due to moving image data can be reduced. The transfer timing may be scheduled in advance, or may be the timing when any new moving image is recorded, or may be the timing when the free space of the storage unit 104 becomes a predetermined value or less.

Further, the tablet terminal 10 and the station 20 can cancel and change the subject EP linked to the device 40 (personal information held in the device 40). Since the subject EP leaves the hospital on a regular basis, the device 40 of this subject EP is no longer necessary after he/she leaves the hospital. Accordingly, it is necessary to cancel the link between the device 40 and the subject EP who left the hospital and link the new subject EP to the device. For example, once patient card registration is selected in the menu screen, the control unit 102 executes processing of cancelling the subject EP currently linked to the device 40 and linking the new subject EP to the device 40. More specifically, the control unit 102 sends the station 20 personal information including the patient number of the subject EP to be newly linked to the device 40. The pairing reader 201 of the station 20 updates the personal information stored in the storage unit 401 of the device 40 with the new personal information received from the tablet terminal 10. Thereby, the subject EP linked to the device 40 is changed.

Figure 11:
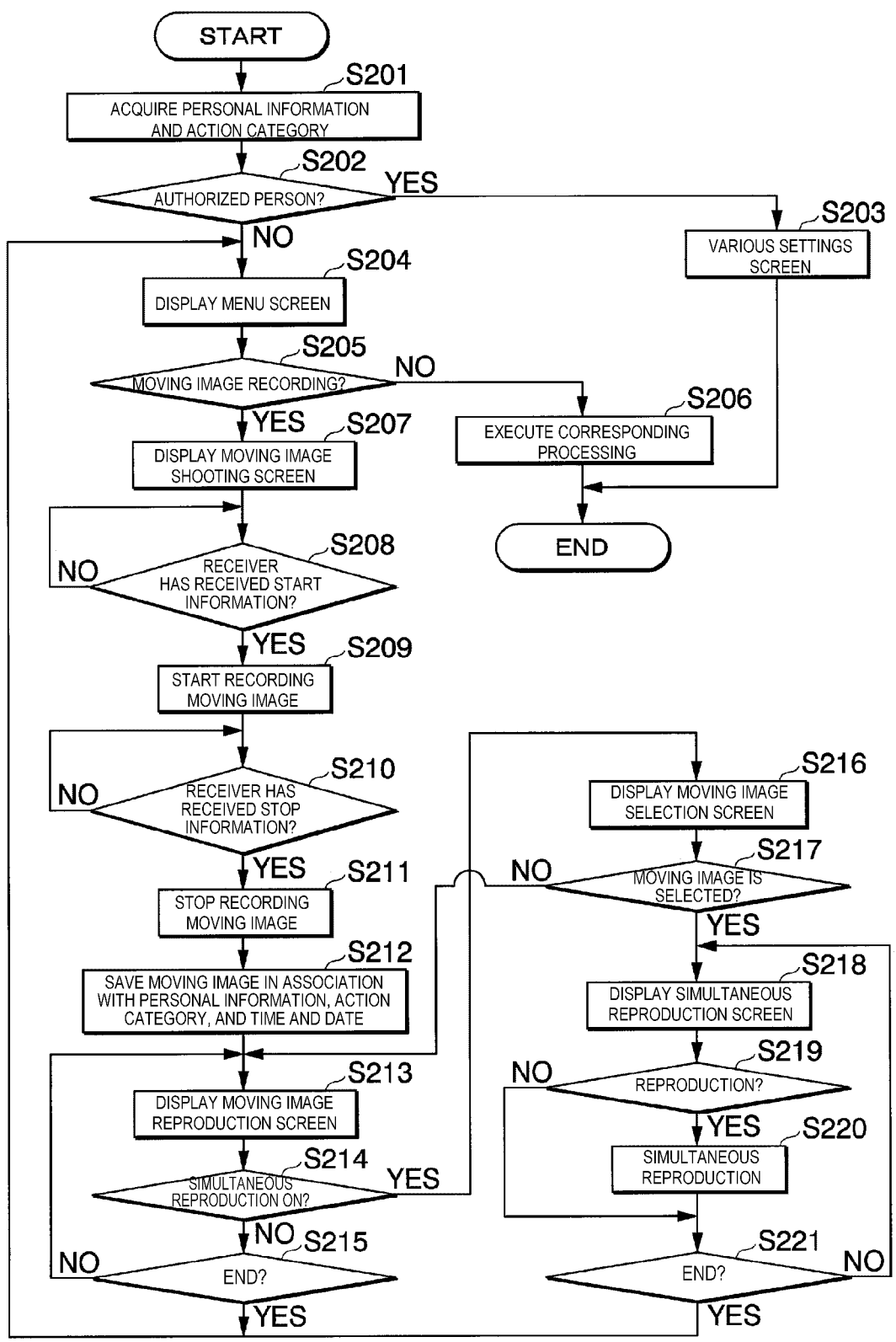
FIG. 11 is a flowchart illustrating an example of moving image record reproduction processing executed by the tablet terminal in the first embodiment of the present invention.

FIG. 11 is a flowchart illustrating an example of moving image record reproduction processing executed by the tablet terminal 10. This drawing illustrates processing of the tablet terminal 10 taking and recording a moving image of the subject EP and reproducing the recorded moving image. The tablet terminal 10 executes the processing illustrated in this drawing upon receipt of personal information and an action category from the station 20.

First, the helper SP places the device 40 in front of the pairing reader 201 of the station. Once the device 40 is placed in front of the pairing reader 201, the station 20 reads personal information from the device 40, and sends the tablet terminal 10 the read personal information and the action category corresponding to the read area over which the device 40 is placed.

(Step S201) The control unit 102 receives and acquires the personal information and the action category from the station 20 via the connection unit 107. Then, the process moves to processing in Step S202.

(Step S202) The control unit judges whether or not the personal information thus received is the personal information of an authorized person. The authorized person denotes a person who is authorized to manipulate the tablet terminal 10, e.g. the helper SP. If the control unit 102 judges that the personal information is the personal information of an authorized person, the process moves to processing in Step S203. On the other hand, if the control unit 102 judges that the personal information is the personal information of an unauthorized person (i.e. the subject EP), the process moves to Step S204.

(Step S203) The control unit 102 displays, on the display unit 103, a various settings screen showing kinds of processing that an authorized person can manipulate, and executes the kind of processing specified by the authorized person. The kinds of processing that the authorized person can manipulate include checking of a moving image of the subject EP, comparison between moving images of the subject EP, and deletion of a moving image, for example. Note that, the system may have such a configuration that there are several types of authorities and executable processing differs according to the types, e.g. a first authorized person can check, compare, and delete moving images of all the subject Eps while a second authorized person can check, compare, and delete moving images of the subject EP who the second authorized person takes care of only. Then, the processing terminates.

(Step S204) The control unit 102 displays a menu screen on the display unit 103. Items displayed on the menu screen include moving image recording, moving image reproduction, moving image transfer, patient card registration, and logout.

Then, the process moves to Step S205.

(Step S205) The control unit 102 judges whether or not moving image recording is selected in the menu screen. If the control unit 102 judges that moving image recording is selected, the process moves to Step S207. On the other hand, if the control unit 102 judges that moving image recording is not selected, the process moves to Step S206.

(Step S206) The control unit 102 executes the processing selected in the menu screen. Then, the processing terminates.

(Step S207) The control unit 102 initiates the imaging unit 101, and displays a moving image shooting screen on the display unit 103. Then, the process moves to processing in Step S208.

(Step S208) The control unit 102 judges whether or not the receiver 106 has received start information from the remote controller 30. If the control unit 102 judges that the receiver has received the start information, the process moves to processing in Step S209. On the other hand, if the control unit 102 judges that the receiver has not received the start information, the process executes the processing in Step S208 again.

(Step S209) The control unit 102 starts recording the moving image taken by the imaging unit 101. Then, the process moves to processing in Step S210.

(Step S210) The control unit 102 judges whether or not the receiver 106 has received stop information from the remote controller 30. If the control unit 102 judges that the receiver has received the stop information, the process moves to processing in Step S211. On the other hand, if the control unit 102 judges that the receiver has not received the stop information, the process executes the processing in Step S210 again.

(Step S211) The control unit 102 stops recording the moving image. Then, the process moves to processing in Step S212. Note that, the system may have such a configuration that people can edit the moving image before stopping recording the moving image, e.g. the control unit stops recording the moving image and the process moves to processing in Step S212 after people rotates the orientation of the moving image or trims the moving image.

(Step S212) The control unit 102 writes and saves the recorded moving image in the storage unit 104 in association with the personal information and the action category acquired in Step S201 and the time and date when the recording ends. Then, the process moves to processing in Step S213.

(Step S213) The control unit 102 displays, on the display unit 103, a moving image reproduction screen for reproducing the recorded moving image. Then, the process moves to processing in Step S214.

(Step S214) The control unit 102 judges whether or not the simultaneous reproduction ON button is pressed in the moving image reproduction screen and its input is accepted. If the control unit 102 judges that its input is accepted, the process moves to processing in Step S216. On the other hand, if the control unit 102 judges that its input is not accepted, the process moves to processing in Step S215.

(Step S215) The control unit 102 judges whether or not the end button is pressed in the moving image reproduction screen and its input is accepted. If the control unit 102 judges that its input is accepted, the process moves back to the processing in Step S204. On the other hand, if the control unit 102 judges that its input is not accepted, the process moves back to the processing in Step S213.

(Step S216) The control unit 102 displays a moving image selection screen on the display unit 103. Then, the process moves to processing in Step S217.

(Step S217) The control unit 102 judges whether or not a moving image to be simultaneously reproduced is selected in the moving image selection screen. If the control unit 102 judges that the moving image to be simultaneously reproduced is selected, the process moves to processing in Step S218. On the other hand, if the control unit 102 judges that no moving image to be simultaneously reproduced is selected, the process moves back to the processing in Step S213.

(Step S218) The control unit 102 displays, on the display unit 103, a simultaneous reproduction screen for reproducing the moving image selected in the moving image selection screen and the recorded moving image at the same time. Then, the process moves to processing in Step S219.

(Step S219) The control unit 102 judges whether or not the reproduction button is pressed in the simultaneous reproduction screen and its input is accepted. If the control unit 102 judges that its input is accepted, the process moves to processing in Step S220. On the other hand, if the control unit 102 judges that its input is not accepted, the process moves to processing in Step S221.

(Step S220) The control unit 102 reproduces the selected moving image and the recorded moving image at the same time. Then, the process moves to processing in Step S221.

(Step S221) The control unit 102 judges whether or not the end button is pressed in the simultaneous reproduction screen and its input is accepted. If the control unit 102 judges that its input is accepted, the process moves back to the processing in Step S204. On the other hand, if the control unit 102 judges that its input is not accepted, the process moves back to the processing in Step S218.

As has been described above, the rehabilitation support system S1 in this embodiment includes: the portable tablet terminal 10; and the station 20 to and from which the tablet terminal 10 is attachable and detachable. The station 20 includes: the first connection unit 204 configured to be connected to the tablet terminal 10 and transmit and receive data to and from the tablet terminal when the tablet terminal 10 is attached to the station; the pairing reader 201 configured to acquire subject identification information for identifying the rehabilitation subject; and the control unit 203 configured to send the subject identification information, acquired by the pairing reader 201, to the tablet terminal 10 via the first connection unit 204. The tablet terminal 10 includes: the connection unit 107 configured to be connected to the station 20 and transmit and receive data to and from the station when the tablet terminal is attached to the station; the imaging unit 101 configured to take an image of the subject; the storage unit 104 configured to store a moving image taken by the imaging unit 101; and the recording controller 1021 configured to receive the subject identification information from the station 20 via the connection unit 107, and writes the moving image of the subject, taken by the imaging unit 101, in the storage unit 104 in association with the subject identification information thus received.

According to the above configuration, the subject identification information acquired by the station 20 is automatically associated with the moving image and stored in the tablet terminal 10. This enables the taken moving image of the subject EP to be stored on a per-subject basis by simple manipulation. Accordingly, the helper SP does not need to check moving images and sort them by subjects after his/her work is over, thereby improving operability.

In the field of rehabilitation, in particular, moving images are typically recorded and managed in the following procedure. First, in order to conduct fixed-point observation of a rehabilitation action, the helper SP installs a video camera on a tripod and take images of the action of the subject EP during rehabilitation. The helper SP checks the taken moving images immediately after the images are taken, and clears up the tripod if there is no problem with the images. After the rehabilitation is over, the helper removes a recording medium from the video camera, and makes a copy of the moving image data to a personal computer. Then, while visually checking the taken moving images in the personal computer, the helper updates records such as a rehabilitation subject name and which action the subject has performed and sorts folders, for example. In this way, there is a problem with the existing moving image recording and management in that it has a lot of work processes and is thus troublesome. In addition, since the helper SP registers and organizes moving images after he/she finishes the daytime work such as rehabilitation, the helper SP sometimes finishes work late. The rehabilitation support system S1 of this embodiment makes it possible to improve operability in a moving image recording system, and reduce the time and burden required for the helper SP to work.

In addition, in the rehabilitation support system S1 of this embodiment, the pairing reader 201 acquires a rehabilitation-related action category together with subject identification information, the control unit 203 sends the action category together with the subject identification information to the tablet terminal 10 via the first connection unit 204, and the recording controller 1021 writes a moving image in the storage unit 104 while associating it with the subject identification information and action category thus received. According to the above configuration, the subject identification information and action category acquired by the station 20 are automatically associated with the moving image and stored in the tablet terminal 10. This makes it possible to store, by simple manipulation, moving images of the subject EP while sorting them by subjects and action categories. Thereby, the helper SP does not need to check moving images and sort them by action categories after his/her work is over, thus improving operability.

Moreover, in the rehabilitation support system S1 of this embodiment, the pairing reader 201 reads subject identification information from the device 40 that stores the subjection identification information therein. Thereby, it is possible to input subject identification information into the station 20 and the tablet 10 by simple manipulation of placing the device 40 in front of the pairing reader 201.

Besides, in the rehabilitation support system S1 of this embodiment, the pairing reader 201 is provided for each action category with the read area for reading subject identification information from the device 40 storing the subject identification information, and acquires an action category according to the read area where the subject identification information is read. Thereby, it is possible to input subject identification information and an action category into the station 20 and the tablet terminal 10 by simple manipulation of placing the device 40 in front of the read area corresponding to a rehabilitation action category that the subject EP is going to do.

Further, in the rehabilitation support system. S1 of this embodiment, the tablet terminal 10 includes the display unit 103 configured to reproduce and display a moving image stored in the storage unit 104, and the display controller 1022 configured to reproduce multiple moving images of the subject EP at the same time while displaying them on the display unit 103 side by side. According to the above configuration, it is possible to reproduce multiple moving images stored in the tablet terminal 10 at the same time while displaying them side by side. Hence, by reproducing two moving images at the same time and comparing them with each other, for example, it is possible to compare the current rehabilitation behavior with the past one easily. Thereby, it is possible to present the subject EP or the helper SP with a rehabilitation effect, a recovery state, and the like more intuitively.

Furthermore, in the rehabilitation support system. S1 of this embodiment, the tablet terminal 10 includes the reproduction position specification unit (the reproduction location bars BR1, BR11, and BR21 and the end location bars BR2, BR12, and BR22) which specifies a reproduction position of the moving image, and the display controller 1022 reproduces a moving image at a reproduction position specified by the reproduction position specification unit. According to the above configuration, it is possible to adjust the reproduction position of each of moving images to be reproduced at the same time. Accordingly, it is possible to reproduce multiple moving images at the same time while adjusting the reproduction position of each moving image to its action start timing, for example, and thus compare the multiple moving images more easily.

MODIFIED EXAMPLE

Next, a modified example of the first embodiment is described.

Figure 12:
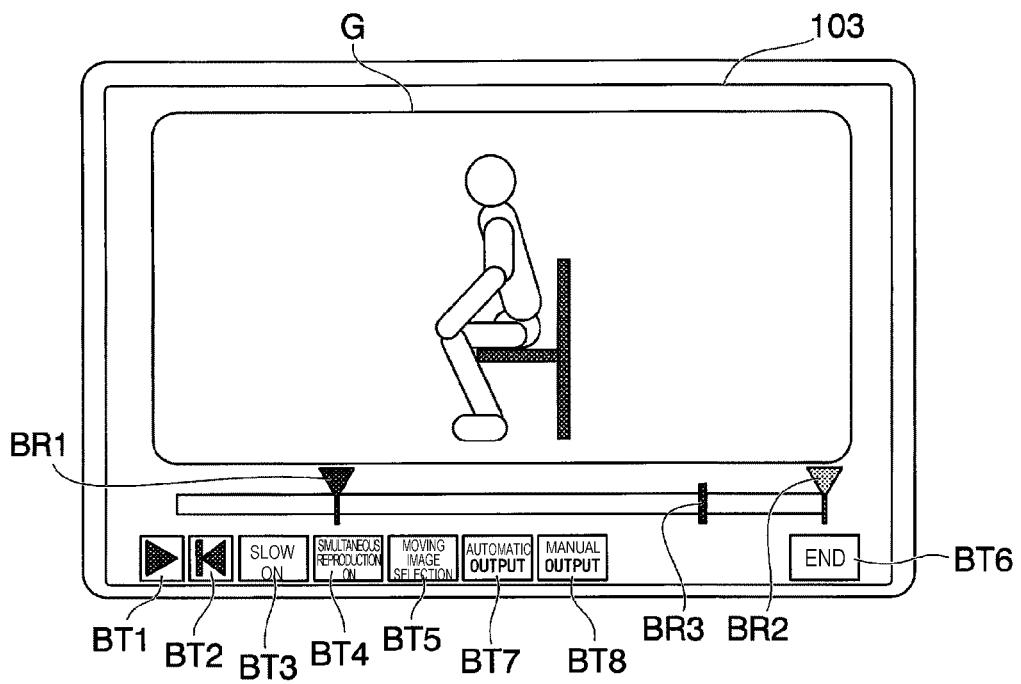
FIG. 12 is a conceptual view illustrating an example of a moving image reproduction screen displayed on the display unit of the tablet terminal in the modified example.

FIG. 12 is a conceptual view illustrating an example of a moving image reproduction screen displayed on the display unit 103 of the tablet terminal 10 in this modified example. In the moving image reproduction screen illustrated in this drawing, as in FIG. 8, the reproduction area G for reproducing a moving image, the reproduction button BT1 for reproducing a moving image, the reset button BT2 for resetting the current reproduction position to the reproduction start position, the slow ON button BT3 for reproducing a moving image at a slow rate, the simultaneous reproduction ON button BT4 for reproducing multiple moving images at the same time, the moving image selection button BT5 for selecting a moving image to be reproduced, and the end button BT6 for ending the moving image reproduction screen and moving back to the original screen are arranged.

Further, in the moving image reproduction screen, as in FIG. 8, the reproduction location bar BR1, the end location bar BR2, and the current position bar BR3 are arranged below the reproduction area G. In addition, in this modified example, an automatic OUTPUT button BT7 for automatically dividing a moving image into a predetermined number of still images, and a manual OUTPUT button BT8 for dividing a moving image into multiple still images the number of which is specified by the helper SP are arranged side by side with the various buttons.

Once the automatic OUTPUT button BT7 is pressed in the moving image reproduction screen and its input is accepted, the display controller 1022 of the control unit 102 extracts a predetermined number of still images from a moving image in a range between the position specified by the reproduction location bar BR1 and the position specified by the end location bar BR2. The predetermine number may be previously set, or may be specified by the helper SP before or after he/she presses the automatic OUTPUT button BT7. Besides, still images may be extracted at equal time intervals, or may be extracted at time intervals based on a predetermined ratio. The display controller 1022 displays the extracted still images on the display unit 103 side by side. To extract a predetermined number of still images from a moving image and display them is also referred to as automatic OUTPUT.

Once the manual OUTPUT button BT8 is pressed in the moving image reproduction screen and its input is accepted, the display controller 1022 of the control unit 102 extracts, from a moving image, a still image corresponding to the time when the input is accepted, and displays it on the display unit 103. If the manual OUTPUT button BT8 is pressed multiple times, the display controller 1022 displays extracted still images on the display unit 103 side by side. To extract a still image specified by the helper SP from a moving image and display it is also referred to as manual OUTPUT.

Figure 13:
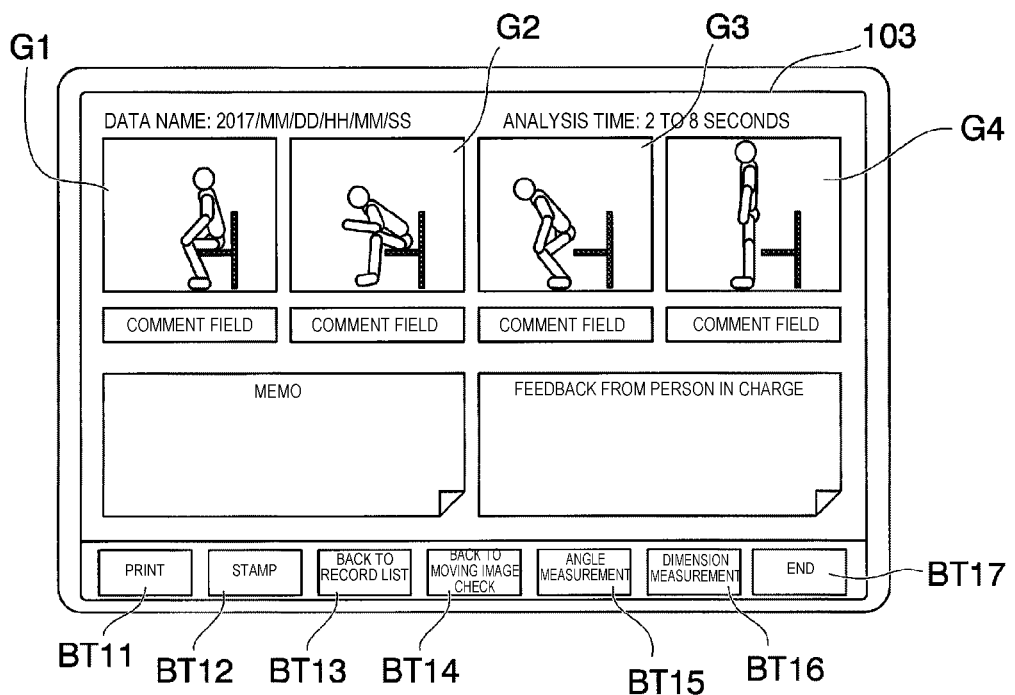
FIG. 13 is a first conceptual view illustrating an example of an automatic OUTPUT screen displayed on the display unit of the tablet terminal in the modified example.

FIG. 13 is a first conceptual view illustrating an example of an automatic OUTPUT screen displayed on the display unit 103 of the tablet terminal 10 in this modified example.

A data name and an analysis period are displayed in an upper part of the display unit 103. The data name indicates a name for identifying data, and is the year, month, day, hour, minute, and second when automatic OUTPUT is executed. The analysis period indicates a reproduction period of a moving image corresponding to a range in which still images are extracted.

Multiple still images extracted are displayed in the display unit 103. In the example of this drawing, still images G1 to G4 are displayed side by side in chronological order. A comment field is provided below each of the still images G1 to G4, and a person can leave and display a comment therein for any characteristic action scene. In addition, various fields where a person can write a memo and a feedback from the person in charge are also displayed. Further, the system may have such a configuration that one or more vertical and horizontal grid lines are displayed in each still image and grid line display positions are synchronized between the still images, e.g. horizontal and vertical grid lines are respectively displayed at the positions of a seating face and a body trunk observed when a subject is seated at the time of action start. This facilitates checking when current and past standing and sitting actions are compared for example, such as "a subject takes a better forward tilting posture than before" and "his/her posture is stable". Furthermore, the system may have such a configuration that characteristic action scenes are displayed with markers written thereon in each of the still images G1 to G4.

A print button BT11, a stamp button BT12, a record list button BT13, a moving image check button BT14, an angle measurement button BT15, a dimension measurement button BT16, and an end button BT17 are arranged in a lower part of the display unit 103. By pressing the print button BT11, the content displayed on the display unit 103 can be printed and output on paper. By pressing the stamp button BT12, a sign such as an arrow is displayed, and it is possible to point an important portion and the like by moving this sign to any desired location in the display unit 103. By pressing the record list button BT13, the screen transitions to a screen for displaying a list of recorded moving images. By pressing the moving image check button BT14, the screen transitions to a screen for reproducing a selected moving image. By pressing the angle measurement button BT15, it is possible to draw two lines in the screen and measure the internal angle between these lines. Thereby, it is possible to measure an angle at the time when a subject raises his/her arm, a tilt angle of his/her body trunk, and the like in a simplified method. By pressing the dimension measurement button BT16, it is possible to input a reference dimension of a portion that shows up in a still image, and measure its dimension in the still image based on the reference dimension in a simplified method. The reference dimension indicates the length of a portion whose length is measured in advance. For example, by selecting an arm portion in the still image and inputting the arm length previously measured, it is possible to measure the dimension in the still image with this input length used as a reference. By pressing the end button BT17, the application ends. Note that, in this example, a button for outputting and saving the display content as data may be disposed instead of or in addition to the print button BT11.

In this way, by extracting a predetermined number of still images from a taken rehabilitation action moving image and displaying them, it is possible to have a look through them and check a change in action, and thus improve efficiency of checking the rehabilitation action. In the rehabilitation scene, in particular, paper medical records are often used as communication means. Heretofore, images of a moving image have sometimes been cut out and pasted onto a material sheet one by one; however, it requires a lot of work and is inefficient. In the rehabilitation support system S1 according to this modified example, it is possible to extract a predetermined number of still images from a moving image and display them by pressing the automatic OUTPUT button BT7, and possible to output them in the form of a sheet by pressing the print button BT11. Thus, by using this sheet which is output together with the medical record, it is possible to facilitate checking work at the scene. In addition, by outputting them as data, it is possible to facilitate subsequent work such as preparation of materials.

Figure 14:
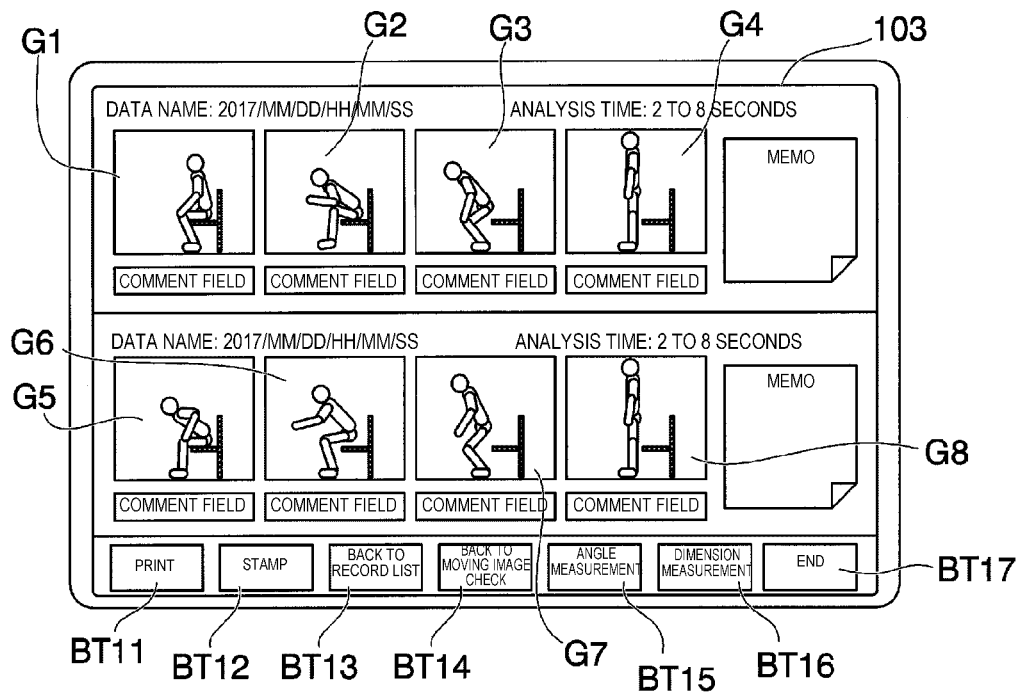
FIG. 14 is a second conceptual view illustrating an example of the automatic OUTPUT screen displayed on the display unit of the tablet terminal in the modified example.

FIG. 14 is a second conceptual view illustrating an example of the automatic OUTPUT screen displayed on the display unit 103 of the tablet terminal 10 in this modified example. The display unit 103 is divided into upper and lower rows. In the upper row, still images G1 to G4 extracted by the display controller 1022 from a recorded rehabilitation action moving image are displayed side by side. In the lower row, still images G5 to G8 extracted by the display controller 1022 from a moving image different from that in the upper row are displayed. By displaying the still images in the upper and lower rows in one screen, it is possible to easily compare actions extracted from multiple moving images. Note that the display controller may extract still images of different reproduction ranges from the same moving image. In addition, at the time of comparison, the display unit 103 may be divided into not only two upper and lower rows but also right and left columns, or may be divided into three or more rows/columns to display three or more still image groups. Further, memo and comment fields and the like may be arranged as in the example of FIG. 13, or may be arranged with different layout as appropriate.

In this way, by extracting a predetermined number of still images from multiple rehabilitation action moving images taken and displaying the predetermined number of still images thus extracted on the display unit 103, it is possible to have a look through and compare multiple actions, and easily know how the rehabilitation action is improved.

Second Embodiment

Figure 15:
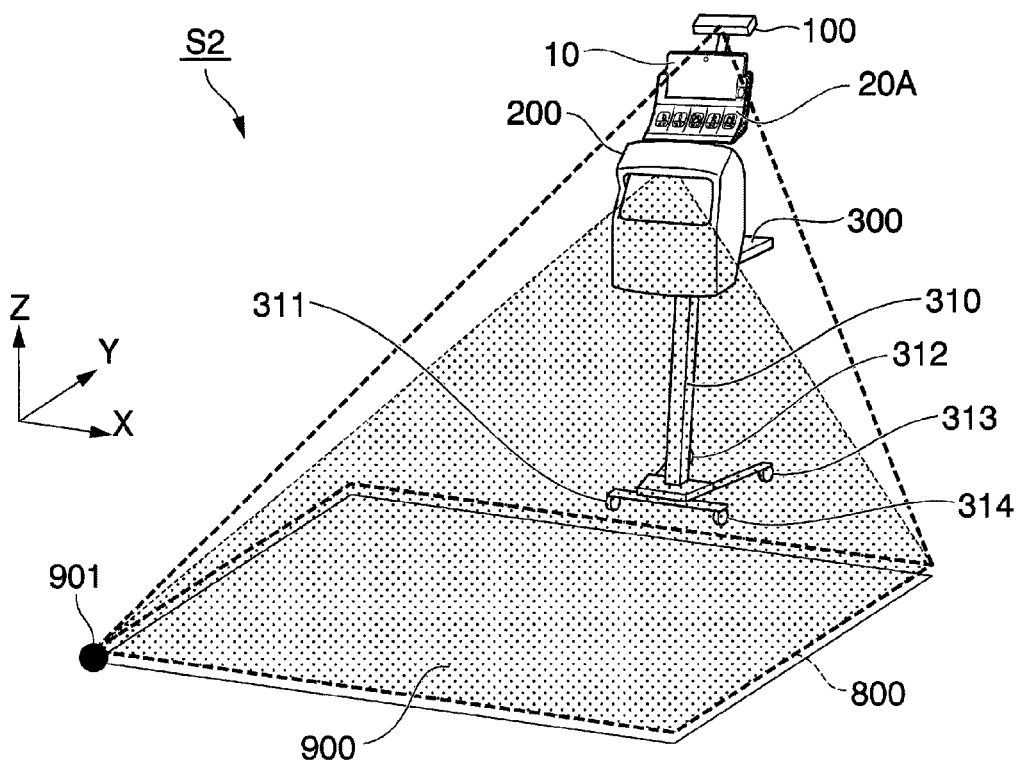
FIG. 15 is a perspective view illustrating the system configuration of a rehabilitation support system in a second embodiment of the present invention.

Next, a second embodiment is described. FIG. 15 is a perspective view illustrating the system configuration of a rehabilitation support system S2 (moving image recording system) according to this embodiment. The rehabilitation support system S2 is a system that provides support for rehabilitation on the subject to undergo rehabilitation EP. The rehabilitation support system S2 includes: the tablet terminal 10; a station 20A; a sensor 100; an output device 200; and a rehabilitation support apparatus 300.

The sensor 100 is configured to detect the subject EP within a detection range 800 of the sensor 100 (within a range surrounded by a broken line of FIG. 15). The sensor 100 is a sensor, such as an image sensor, an infrared sensor, a laser sensor, and a thermosensor, capable of detecting the motion of the subject EP without a marker mounted on the subject EP. In this embodiment, a description is given while the case of using Kinect (registered trademark), embedded with a distance sensor and an image sensor, as the sensor 100 is taken as an example of such a sensor.

The sensor 100 includes an image sensor (not illustrated), for example. The image sensor has: (1) a function of a moving image camera configured to take images of a view in its front direction in real time and acquire multiple sequential two-dimensional images (frame images); and (2) a function of a distance sensor (depth sensor) configured to acquire distance information (an image showing distance information) from the sensor 100 to an actual position corresponding to each position in the two-dimensional images (frame images). With the function of the distance sensor, this image sensor acquires a taken image of the subject EP and distance image information which is information on coordinates in a three-dimensional space of each body portion of the subject EP in the taken image. The three-dimensional space detected by the sensor 100 is a space represented by an XYZ orthogonal coordinate system illustrated in FIG. 15.

Each body portion of the subject EP is a body portion required to be detected in order to recognize the action of the subject EP. Specifically, each body portion of the subject EP indicates the position of a body portion such as a head, shoulders, arms, hands, waist, feet, and joint portions of the subject EP, for example.

The sensor 100 outputs information on a detection result (hereinafter referred to as "detection result information") to the rehabilitation support apparatus 300. The detection result information is information on the position of a part of the body of the subject EP, for example.

Note that, the sensor 100 may be a sensor configured to detect the subject EP by detecting a marker mounted on the subject EP.

The output device 200 is configured to output an image on rehabilitation executed on the subject EP. The output device 200 is an image projection device such as a projector, for example. The output device 200 projects an image for supporting rehabilitation and displays it in an output area 900. Examples of such an output image include an image that contains a movement history of the position of a part of the body of the subject EP and a movement target position of the part of the body of the subject EP. For example, in the case of walking rehabilitation, the system may have such a configuration that the output device 200 displays any one of or both of a movement history of the position of the feet of the subject EP and a target position for the subject EP to move his/her feet to. Meanwhile, in the case of hand movement rehabilitation, the system may have such a configuration that the output device 200 displays any one of or both of a movement history of the position of the hands of the subject EP and a target position for the subject EP to move his/her hands to. In the following description, an image representing a movement history of the position of a part of the body of the subject EP is referred to as a history image. On the other hand, an image representing a movement target position of the part of the body of the subject EP is referred to as a target image.

The rehabilitation support apparatus 300 is constituted of an information processor. Specifically, the rehabilitation support apparatus 300 includes a CPU, a memory, and an auxiliary storage device which are connected to each other via a bus. The rehabilitation support apparatus 300 operates by executing a rehabilitation support program. The rehabilitation support apparatus 300 executes an application related to rehabilitation to be performed by the subject.

The tablet terminal 10 is a portable tablet type information processor. The tablet terminal 10 is attachable to the station 20A and detachable from the station 20A.

The station 20A is a station to and from which the tablet terminal 10 is attachable and detachable. The station 20A keeps the tablet terminal 10 in a standing position with its front face facing the front. The station 20A is installed in such a position that the tablet terminal 10 can take an image of the subject EP when the tablet terminal 10 is attached (e.g.

above the rehabilitation support apparatus 300). In addition, when the tablet terminal 10 is attached, the station 20A is connected to the tablet terminal 10 to transmit and receive data. Further, the station 20A is connected to a power supply, and supplies power to the tablet terminal 10 automatically once the tablet terminal 10 is attached.

The sensor 100 and the like are supported by a leg unit 310. The leg unit 310 is expandable and contractible in an up-down direction, and is capable of adjusting a height position of the sensor 100 and the output device 200. Thereby, it is possible to adjust the amplitude of the detection range of the sensor 100. In addition, in the case where the output device 200 is a projection device, it is possible to adjust the amplitude of the output range 900. Besides, the leg unit 310 includes casters 311, 312, 313, and 314. Since the casters 311, 312, 313, and 314 are rotatable, it is possible to freely move the rehabilitation support system S2 on a floor by pushing it by hand.

Figure 16:
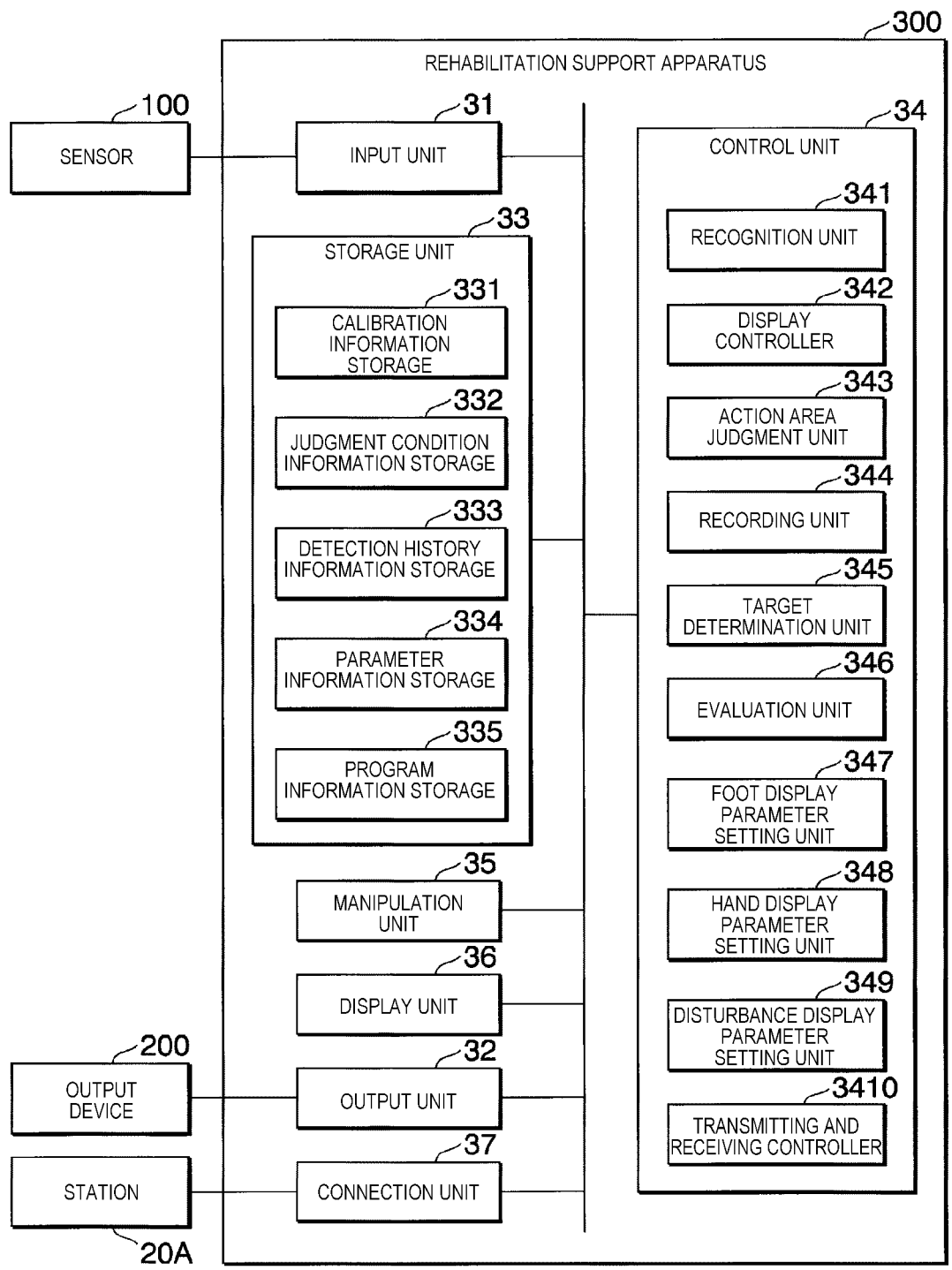
FIG. 16 is a schematic block diagram illustrating a functional configuration example of a rehabilitation support apparatus equipped in the rehabilitation support system in the second embodiment of the present invention.

FIG. 16 is a schematic block diagram illustrating a functional configuration example of the rehabilitation support apparatus 300 equipped in the rehabilitation support system S2. The rehabilitation support apparatus 300 includes: an input unit 31; an output unit 32; a storage unit 33; a control unit 34; a manipulation unit 35; a display unit 36; and a connection unit 37.

The input unit 31 is an interface for inputting information from the outside. For example, the input unit 31 acquires information indicating a detection result (detection result information) from the sensor 100.

The output unit 32 is an interface for outputting an image, generated by the control unit 34, to the output device 200.

The storage unit 33 is constituted of a storage device such as a magnetic hard disk device and a semiconductor storage device. The storage unit 33 includes: a calibration information storage 331; a judgment condition information storage 332; a detection history information storage 333; a parameter information storage 334; and a program information storage 335.

The calibration information storage 331 stores calibration information therein. The calibration information is information that associates a coordinate system of coordinates, indicating a detection result of the sensor 100, with a coordinate system on an image plane projected by the output device 200. Accordingly, the calibration in the rehabilitation support apparatus 300 indicates processing of: comprehending the positional relationship between the detection range 800 of the sensor 100 and the image output area 900 of the output device 200; and setting their common coordinate system. Note that the sensor 100's detectable range may be larger than the detection range 800 illustrated. The detection range 800 in this embodiment indicates a detection range required to acquire positional information on a part of the body of the subject EP, which is a detection target part, during action of the subject EP performed inside the output area 900. Note that, "inside the output area 900" includes not only a planar area defined by the output area 900 but also a space inside the output area 900 up to a predetermined height with respect to this area. The calibration information may be obtained by executing calibration in advance, for example.

Once the output device 200 projects marker images, the sensor 100 outputs the position of each marker image to the rehabilitation support apparatus 300 in the form of coordinates in the coordinate system of the sensor 100 (the coordinate system that the sensor 100 uses to show a detection position). Thereby, the rehabilitation support apparatus 300 (the control unit 34) acquires the position of each marker in the form of both the coordinates in the coordinate system of the sensor 100 and the coordinates in the coordinate system of the output device 200. In addition, by means of marker images projected at four corners, for example, the rehabilitation support apparatus 300 (the control unit 34) comprehends coordinates, indicating the range of the output area 900, in the coordinate system of the output device 200. Thereby, a target determination unit 345 to be described later can calculate a target position inside the output area 900 in the coordinate system of the output device 200.

Based on the coordinates thus acquired, the rehabilitation support apparatus 300 (the control unit 34) acquires, as calibration information, information for correcting the coordinate system of the sensor 100. In the case where the sensor 100 has a coordinate system adjustment function, the rehabilitation support apparatus 300 (the control unit 34) uses this function to generate calibration information for aligning the coordinate system of the sensor 100 with the coordinate system of the output device 200. Alternatively, in the case where the output device 200 has a coordinate system adjustment function, the rehabilitation support apparatus 300 (the control unit 34) may use this function to generate calibration information for aligning the coordinate system of the output device 200 with the coordinate system of the sensor 100.

In the case where marker images are hard to detect by the sensor 100, such as when light scatters on a floor face and the marker images blur thereon, the helper SP may detect positions manually instead of position detection using the marker images. In a state where the output device 200 projects an image on the entire output area 900, the sensor 100 takes an image of an area including the entire projection image using its image sensor. The rehabilitation support apparatus 300 displays the image, taken by the sensor 100, on a display screen. Then, the helper SP specifies, with touch manipulation, each of the four corners of the output area 900 displayed on a monitor screen.

Since the image displayed on the monitor screen is the image taken by the sensor 100, the apparatus can acquire the positions, specified by the helper SP, in the form of coordinates in the coordinate system of the sensor 100. The rehabilitation support apparatus 300 (the control unit 34) acquires calibration information based on these coordinates and the coordinates of the four corners of the output area 900 in the coordinate system of the output device 200. Note that the coordinates of the floor are used as coordinates in a height direction. Alternatively, the helper SP may place physical markers, such as cone markers, on the positions of the four corners of the image plane. In this case, the sensor 100 detects the placed markers and outputs the coordinates of each marker.

In the case where the output device 200 projects an image on the floor face, calibration is only needed at the first time the rehabilitation support system 1 is used and is not needed from the second time of use or later. This is because, since neither the positional relationship between the sensor 100 and the floor face nor the positional relationship between the output device 200 and the floor face changes, calibration information acquired at the first time the system is used can be used from the second time of use or later.

The judgment condition information storage 332 is configured to store a condition for judging an action area. The action area will be described later.

The detection history information storage 333 is configured to store a history of positional information (detection result information) on a part of the body of the subject EP recognized by a recognition unit 341. For example, in the case of walking rehabilitation, the detection history information storage 333 stores a history of detection result information on the position of the feet of the subject EP. Meanwhile, in the case of hand movement rehabilitation, the detection history information storage 333 stores a history of detection result information on the position of the hands of the subject EP.

The parameter information storage 334 is configured to store a foot display parameter set by a foot display parameter setting unit 347 to be described later, a hand display parameter set by a hand display parameter setting unit 348 to be described later, and a disturbance display parameter set by a disturbance display parameter setting unit 349 to be described later.

The program information storage 335 is configured to store a rehabilitation support program.

The control unit 34 is constituted of a CPU. By executing the rehabilitation support program, the control unit 34 functions as the recognition unit 341, a display controller 342, an action area judgment unit 343, a recording unit 344, the target determination unit 345, an evaluation unit 346, the foot display parameter setting unit 347, the hand display parameter setting unit 348, the disturbance display parameter setting unit 349, and a transmitting and receiving controller 3410.

The recognition unit 341 is configured to acquire detection result information acquired by the input unit 31 and recognize an object represented by the detection result information. For example, based on the detection result information, the recognition unit 341 recognizes a person, a table, a floor, a wall, and the like that exist inside the detection range 800. For example, by using Kinect (registered trademark), it is possible to recognize the positions of multiple portions of the body of the subject EP. For example, when recognizing a distal end part of a long detection target on a table, the recognition unit 341 detects positional information of this distal end part per unit time. By use of the positional information of these feature points detected by the sensor 100 from moment to moment, the recognition unit 341 recognizes the motion of the position of a part of the body of the subject EP. For example, when detecting a long detection target, the recognition unit 341 recognizes the motion of the position of the distal end of this detection target. This motion of the position of the distal end may be treated as that of the position of the hands of the subject EP.

In addition, the recognition unit 341 may have such a function that, when recognizing an object represented by detection result information as a human being through comparison of the shape of the object with a skeletal model of a human figure, it recognizes the position of each portion of the object. According to this function, the recognition unit 341 can recognize each portion of a human body while associating the positional information of each portion of the human body with this portion. For example, the subject EP stands upright in front of the sensor 100. Then, the recognition unit 341 compares detection result information, obtained by detecting the subject in this state, with the skeletal model of a human figure, and recognizes that this object is a human being because the object has the shape of a human being. The recognition unit 341 also recognizes each portion of the object while associating the positional information of each portion of the object with this portion, such as a left toe with its positional information, a right heel with its positional information, and right and left wrists with their positional information.

By use of the function of recognizing the position of each portion with a skeletal model (hereinafter referred to as the "skeleton tracking function"), the recognition unit 341 can recognize the motion of the position of each portion of the subject EP. In this way, the recognition unit 341 recognizes the position of and the motion of a part of the body of the subject EP by tracking a predetermined position of an object of a predetermined shape included in detection result information or by use of the skeleton tracking function.

Further, by use of Kinect (registered trademark), it is possible to acquire information of the coordinates of each object existing inside the detection range 800 (point group data including information on the coordinates of each object, existing inside the detection range 800, calculated at predetermined intervals). The recognition unit 341 analyzes detection result information (point group data), and recognizes a plane which has a predetermined area or larger and whose Z-coordinate value does not change (i.e. a set of point group whose Z-coordinate value is almost constant) as a plane of a wall, a floor, a table, or the like. In addition, out of the detection result information, the recognition unit 341 recognizes which data is detection data of a part of the body of the subject EP (detection target portion) related to an action area judged by the action area judgment unit 343 to be described later, and selects this data (detection target information).

Here, the action area indicates an area where the subject EP performs an action which is a target for rehabilitation, more specifically, indicates a predetermined area in a space where a portion which is strongly related to an action aiming for recovery by rehabilitation acts. For example, the action area is an area to which the subject EP brings his/her portion closer during rehabilitation. Alternatively, the action area is an area which includes the position of an action goal (destination) of the subject EP during rehabilitation, for example. Still alternatively, the action area is a location where the subject EP performs a target action during rehabilitation, for example. Specific examples of the action area include a floor and a table in the case of a two-dimensional area. For example, a portion which is strongly related to an action aiming for recovery by rehabilitation is feet in the case of a floor, and is hands in the case of a table.

The subject EP brings his/her feet closer to a floor in walking rehabilitation, and brings his/her hands closer to a table in hand movement rehabilitation. Alternatively, for example, a floor is an area which includes the position of a destination of walking (target image display position) in the case of walking rehabilitation, and a table is an area which includes the position of a destination of hands (target image display position) in the case of hand movement rehabilitation. Still alternatively, a floor and a table are locations where the subject performs a target action during walking rehabilitation and during hand movement rehabilitation, respectively.

Note that, specific examples of the action area in the case where the action area is a three-dimensional area include a space within a predetermined height range with respect to a table surface of a table (hereinafter referred to as a "three-dimensional action area"). For example, the output device 200 displays a target image, which denotes "10 cm", on a table. For example, the output device may display "10 cm" on a certain position on the table. This target image denotes that a space right above the position of the table, where the target image is displayed, at a position 10 cm above the table surface is a hand destination position. The position of this target image is included in the three-dimensional action area. In the case of this example, also, the three-dimensional action area indicates an area where a portion (hand) which is strongly related to an action aiming for recovery by rehabilitation acts, for example.

The three-dimensional action area is an area to which the subject brings his/her hands closer during hand movement rehabilitation. Alternatively, the three-dimensional action area is an area which includes the position of a destination of hand movement (target image position). Still alternatively, the three-dimensional action area is a location where the subject EP performs a target action during hand movement rehabilitation. Note that, other examples of the action area in the case where the action area is a three-dimensional area include a space above the output area 900. For example, in the case where the action area is a space above the output area 900, rehabilitation may be carried out in such a manner that a target image is projected on this space and the subject EP touches this target image by hand, for example.

The display controller 342 is configured to generate an image to be output by the output device 200. For example, the display controller 342 generates images such as: a target image displayed in the action area for guiding the subject EP's action; an image including information on a rehabilitation evaluation result; and an image indicating the trajectory of an action of a detection target portion of the subject EP that the subject has performed during rehabilitation.

The action area judgment unit 343 is configured to judge the action area based on a recognition result of the recognition unit 341. As will be described later, the judgment of the action area may be performed in various ways. Based on a predetermined judgment condition, the action area judgment unit 343 judges that the action area is a floor, for example. Alternatively, the action area judgment unit 343 judges that the action area is a table, for example.

Once judging the action area, the action area judgment unit 343 determines a portion to be detected (detection target portion) which is related to the action area of the subject EP. The detection target portion is a part of the body deeply related to a rehabilitation target action. For example, when judging that the action area is a floor, the action area judgment unit 343 determines the ankles of the subject EP as the detection target portion. Alternatively, the action area judgment unit 343 may determine the toes of the subject EP as the detection target portion. Meanwhile, when judging that the action area is a table, for example, the action area judgment unit 343 determines the back of the hands of the subject EP as the detection target portion. Alternatively, the action area judgment unit 343 may determine the fingertips of the subject EP as the detection target portion.

Note that, the detection target portion related to the action area is set in the storage unit 33 in advance, and the action area judgment unit 343 determines the detection target portion on the basis of this information and the action area judged by the judgment unit itself. For the detection target portion, a portion with a large action range in a rehabilitation target action may be set, for example. For example, in the case of walking rehabilitation, the portion with a large action range is the feet of the subject EP (e.g. ankles, toes, and heels). In the case of hand movement rehabilitation, the portion with a large action range is the hands of the subject EP (e.g. wrists, fingertips, and the back of his/her hands).

Alternatively, for the detection target portion, a portion close to the display position of a target image generated by the display controller 342 may be set. For example, in the case of walking rehabilitation, in this embodiment, a target image shaped in the form of a foot is displayed at a position onto which the subject EP is supposed to step out during walking; in this case, the portion close to the display position of the target image is the feet of the subject EP (e.g. ankles, toes, and heels). Meanwhile, in the case of hand movement rehabilitation, a target image is displayed at a position onto which the subject EP is supposed to touch; in this case, the portion close to the display position of the target image is the hands of the subject EP (e.g. wrists, fingertips, and the back of his/her hands).

Note that the recognition unit 341 records data on the detection target portion determined by the action area judgment unit 343 (positional information on a part of the body), which is included in the detection result information, in the detection history information storage 333 via the recording unit 344.

The recording unit 344 is configured to write and record the detection result information in the detection history information storage 333.

The target determination unit 345 is configured to determine, based on the position of a part of the body of the subject EP (detection target portion) recognized by the recognition unit 341, a target position of the part of the body of the subject EP. For example, in the case of walking rehabilitation, the target determination unit 345 determines a movement target position of the feet of the subject EP based on at least one of: the current position of the feet of the subject EP; and the position history of the feet of the subject EP. Specifically, the target determination unit 345 may judge the direction of movement of the subject EP based on the position history of the feet of the subject EP and determine the movement target position according to the direction of movement thus judged. Alternatively, the target determination unit 345 may judge the direction of movement of the subject EP based on the orientation of the feet of the subject EP and determine the movement target position according to the direction of movement thus judged. Still alternatively, the target determination unit 345 may determine the movement target position irrespective of the direction of movement of the subject EP, e.g. in a random direction or toward a predetermined goal position.

The target determination unit 345 may calculate the amount of movement of the detection target portion of the body of the subject EP and determine the movement target position based on the amount of movement thus calculated. For example, in the case where the recognition unit 341 recognizes the position of the feet of the subject EP, the target determination unit 345 calculates the length of stride of the subject EP based on the position history of the feet of the subject EP. Then, the target determination unit 345 sets the movement target position at a position ahead of the current position of the feet of the subject EP by the length of stride. The length of stride of the subject EP indicates the amount of movement of the feet of the subject EP and corresponds to an example of the amount of movement of the detection target portion of the body of the subject EP.

In the case where the recognition unit 341 recognizes the movement of the position of the feet of the subject EP, the target determination unit 345 may detect, as the length of stride, the distance by which the feet of the subject EP move. Alternatively, in the case where the recognition unit 341 recognizes the position of a floor face onto which the subject EP steps his/her foot, the target determination unit 345 may detect, as the length of stride, the distance from the position of the floor face onto which the subject EP steps his/her foot to the position of the floor face onto which the subject steps his/her foot next.

The evaluation unit 346 is configured to evaluate the positional relationship between the position and movement target position of the detection target portion of the body of the subject EP. For example, the evaluation unit 346 calculates the distance between the position of the body portion of the subject EP recognized by the recognition unit 341 and the movement target position determined by the target determination unit 345. Then, the evaluation unit 346 judges whether or not the calculated distance is equal to or smaller than a predetermined threshold. If judging that the distance between the detection target portion of the body of the subject EP and the movement target position is equal to or smaller than the threshold, the evaluation unit 346 evaluates that the detection target portion reaches the target position. On the other hand, if judging that the distance between the detection target portion of the body of the subject EP and the movement target position is larger than the threshold, the evaluation unit 346 evaluates that the detection target portion does not reach the target position.

The distance threshold used by the evaluation unit 346 may be a preset constant shared between multiple subjects EP. Alternatively, the evaluation unit 346 may set the threshold for every subject EP, e.g. set one-tenth of the length of stride of the subject EP as the threshold. In addition, the distance threshold used by the evaluation unit 346 may be a value shared between multiple kinds of rehabilitation, or may be set for every kind of rehabilitation. Further, the threshold may be set at such a magnitude that the threshold for foot movement rehabilitation is larger than that for hand movement rehabilitation.

Besides, the number of phases for the evaluation unit 346 to evaluate the relative positional relationship between the position of a part of the body of the subject EP (detection target portion) and the movement target position is not limited to two phases of: "the detection target portion reaches the target position"; and "the detection target portion does not reach the target position" described above, and may be three or more multiple phases. For example, the evaluation unit 346 may make evaluation with three phases of: "the detection target portion reaches the target position"; "small misalignment"; and "large misalignment" by using not only the threshold for judgment on whether or not the detection target portion reaches the target position but also a threshold for judgment on the magnitude of misalignment in the case where the detection target portion does not reach the target position.

Further, the method for the evaluation unit 346 to evaluate the positional relationship between the position and movement target position of the detection target portion of the body of the subject EP is not limited to the method using a threshold. For example, the evaluation unit 346 may judge whether or not there is an overlap between the position and movement target position of the detection target portion of the body of the subject EP, and evaluate that the detection target position reaches the target position if judging that there is an overlap.

Furthermore, in the case of walking rehabilitation, for example, the system may have such a configuration that the target determination unit 345 determines, on a floor face, the movement target position with a certain area range, then the recognition unit 341 recognizes the position of the foot of the subject EP as the range of the foot shape of the subject EP, and then the evaluation unit 346 judges whether or not there is an overlap between the range determined as the movement target position and the range detected as the position of the foot of the subject EP.

The foot display parameter setting unit 347 is configured to set a foot display parameter in foot movement rehabilitation such as walking. The foot display parameter is a parameter used to display the target image during foot movement of the subject EP.

The hand display parameter setting unit 348 is configured to set a hand display parameter in hand movement rehabilitation. The hand display parameter is a parameter used to display the target image during hand movement of the subject EP.

The disturbance display parameter setting unit 349 is configured to set a disturbance display parameter. The disturbance display parameter is a parameter used to display a disturbance that hinders the rehabilitation subject EP from moving his/her foot or hand to a predetermined target image when the subject moves his/her foot or hand to the target image. Alternatively, the disturbance display parameter is a parameter used to display a disturbance that hinders the rehabilitation subject EP from moving his/her foot or hand for bypassing the target image, which is a bypass target, when the subject moves his/her foot or hand for bypassing the target image.

The transmitting and receiving controller 3410 is configured to transmit and receive data to and from the station 20A via the connection unit 37.

The manipulation unit 35 is constituted of existing input devices such as a keyboard, a pointing device (e.g. a mouse and a tablet terminal), a button, and a touch panel. The manipulation unit 35 is manipulated by the helper SP or the like when he/she inputs instructions to the rehabilitation support apparatus 300. The manipulation unit 35 may be an interface for connecting the input devices to the rehabilitation support apparatus 300. In this case, the manipulation unit 35 inputs input signals, generated in the input devices according to inputs by the helper SP or the like, to the rehabilitation support apparatus 300. The manipulation unit 35 may be constituted as a touch panel integrated with the display unit 36.

The display unit 36 is an image display device such as a CRT (Cathode Ray Tube) display, a liquid crystal display, and an organic EL display. The display unit 36 is configured to display images and characters thereon. The display unit 36 may be an interface for connecting the image display device to the rehabilitation support apparatus 300. In this case, the display unit 36 generates video signals for displaying images and characters, and outputs the video signals to the image display device connected to itself.

The connection unit 37 is an interface that is connected to the station 20A to transmit and receive data to and from the station.

Figures 17, 18:
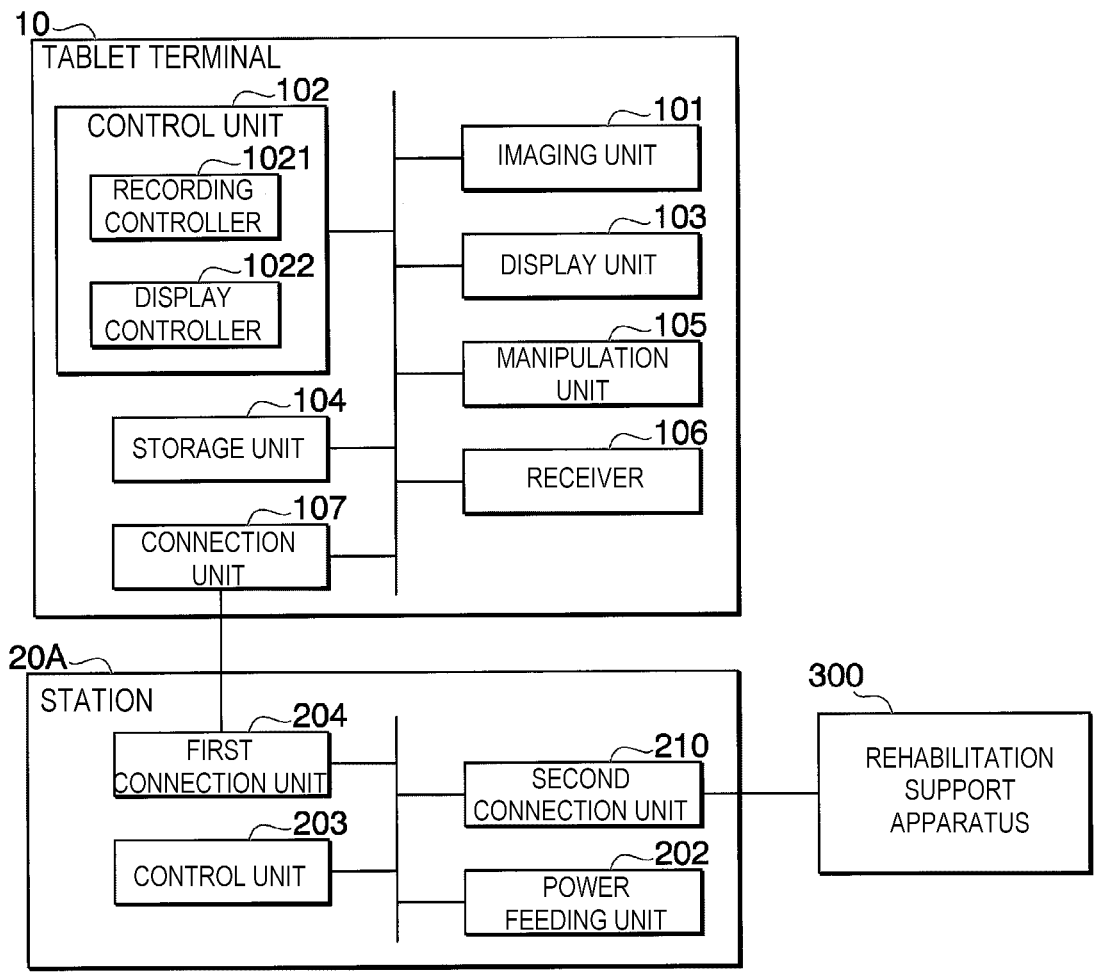
FIG. 17 is a schematic block diagram illustrating a functional configuration example of each of a tablet terminal and a station equipped in the rehabilitation support system in the second embodiment of the present invention.
FIG. 18 is a schematic diagram illustrating the data configuration and a data example of a correspondence table stored in a storage unit of the tablet terminal in the second embodiment of the present invention.

FIG. 17 is a schematic block diagram illustrating a functional configuration example of each of the tablet terminal 10 and the station 20A equipped in the rehabilitation support system S2.

The tablet terminal 10 of this embodiment has the same configuration as that of the first embodiment, and is thus not described here.

The station 20A in this embodiment includes a second connection unit 210 instead of the pairing reader 201 of the station 20 in the first embodiment. The second connection unit 210 is an interface that is connected to the rehabilitation support apparatus 300 to transmit and receive data to and from this apparatus. The second connection unit 210 is an acquisition unit configured to acquire a patient number for identifying the subject EP and his/her rehabilitation-related action category (application name) by receiving them from the rehabilitation support apparatus 300. The configuration of the station 20A other than the above is the same as the configuration of the station 20 in the first embodiment, and is thus not described here.

FIG. 18 is a schematic diagram illustrating the data configuration and a data example of a correspondence table stored in the storage unit 104 of the tablet terminal 10. As illustrated in the drawing, the correspondence table has fields of: a subject; an application name; time and date; and moving image data. The application name is a name of a rehabilitation-related application executed by the subject EP. The resultant image is a data name of a resultant image. Other items are the same as those of the correspondence table in the first embodiment, and are thus not described here.

Figure 19:
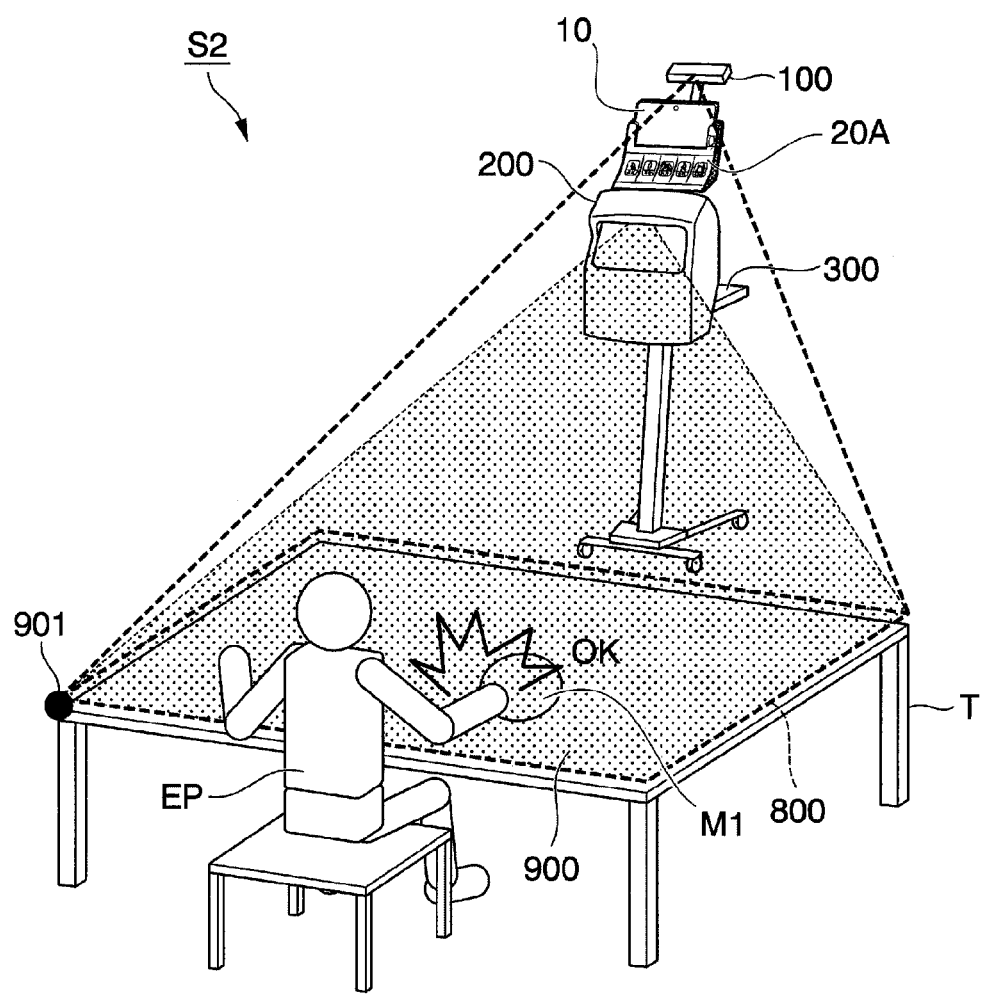
FIG. 19 is a perspective view illustrating how a subject undergoes rehabilitation in the second embodiment of the present invention.
Figure 20:
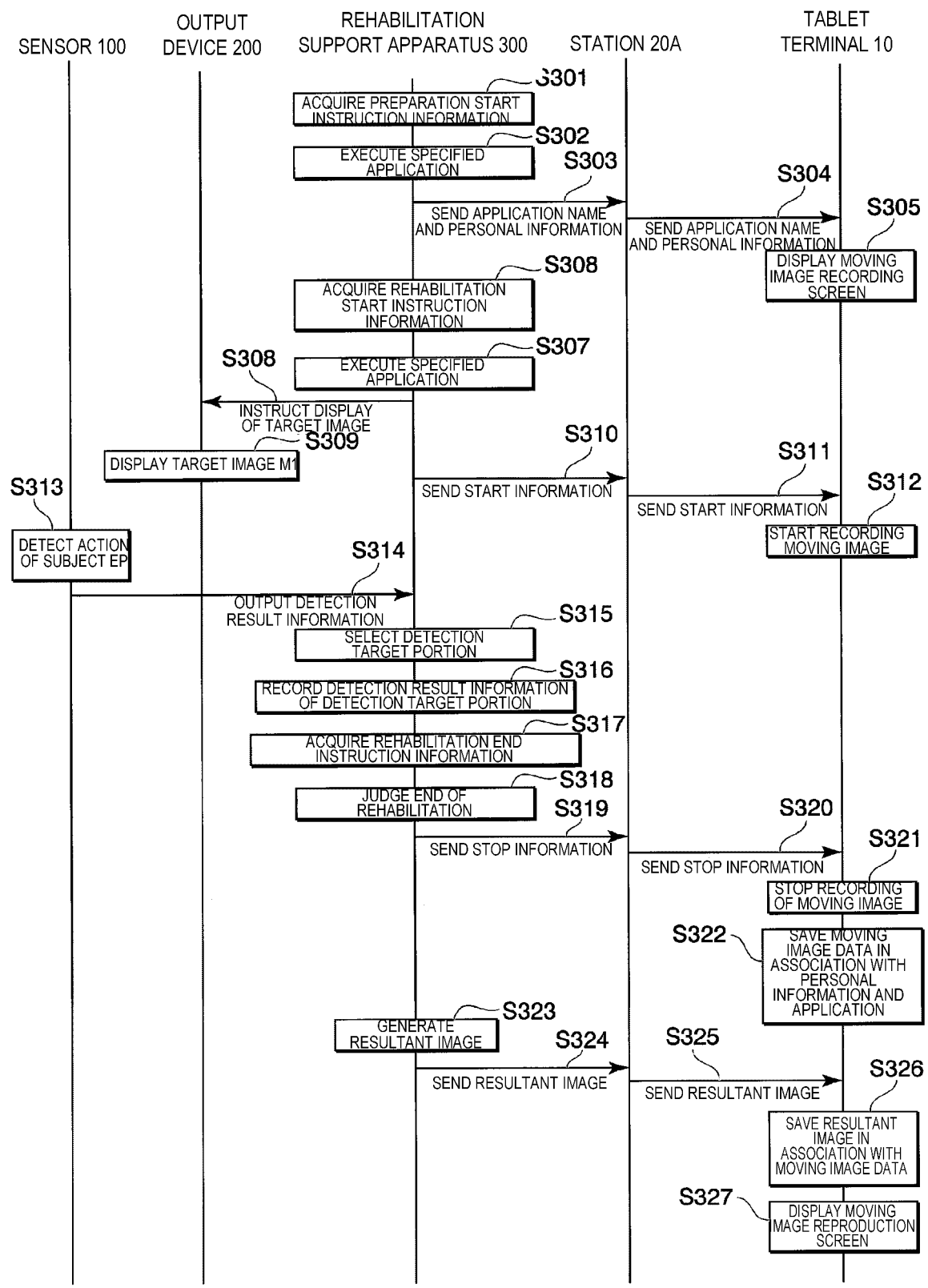
FIG. 20 is a sequence diagram illustrating a processing example in the rehabilitation support system in the second embodiment of the present invention.

Next, the operation of the rehabilitation support system S2 in this embodiment is described with reference to FIGS. 19 and 20. FIG. 19 is a perspective view illustrating how the subject EP undergoes rehabilitation in the rehabilitation support system S2. FIG. 20 is a sequence diagram illustrating a processing example in the rehabilitation support system S2. In the rehabilitation support system S2, it is possible to record how the subject EP undergoes rehabilitation, executed by the rehabilitation support apparatus 300, in the form of a moving image using the tablet terminal 10, and reproduce and check the recorded moving image in the tablet terminal 10.

First, according to the content of rehabilitation the helper SP is to perform, the helper moves the rehabilitation support system S2 to an environment where the subject EP is to undergo rehabilitation, and adjusts the leg unit 310 to a proper height. Then, in the detection range 800, the subject EP takes a posture according to the content of rehabilitation he/she is to undergo. For example, in the case of arm rehabilitation on a table, the subject EP sits on a chair and takes a posture of putting his/her hand on the table. Meanwhile, in the case of walking rehabilitation, for example, the subject EP takes a standing posture.

FIG. 19 illustrates how the subject EP undergoes hand movement rehabilitation on a table T. For example, the subject EP undergoes hand movement rehabilitation based on a target image M1 that is output on the table T (output area 900) by the output device 200. More specifically, the subject EP undergoes hand and arm rehabilitation by chasing, with his/her hands, the position of the target image M1 displayed by the output device 200.

Conditions such as the content of the target image M1, the position where the target image is displayed, and the timing when the target image is displayed differ depending on the rehabilitation content. Applications corresponding to respective kinds of rehabilitation are installed in the rehabilitation support apparatus 300 in advance. The rehabilitation support apparatus 300 displays the target image M1 on the output device 200 by executing the application corresponding to the rehabilitation the subject EP is to undergo.

Once the subject EP takes a rehabilitation start posture, the helper SP inputs preparation start instruction information to the rehabilitation support apparatus 300 together with the personal information of the subject EP such as his/her patient number, name, sex, and height (Step S301). The preparation start instruction information includes information for specifying the application corresponding to the rehabilitation the subject is to undergo. Once the manipulation unit 35 acquires the preparation start instruction information, the control unit 34 of the rehabilitation support apparatus 300 judges the action area, sets parameters used for displaying the target image, and executes the specified application (Step S302). In addition, the transmitting and receiving controller 3410 of the control unit 34 sends the name of the specified application (hereinafter referred to as the "application name") and the personal information of the subject EP (such as the input patient number, name, sex, and height) to the station 20A via the connection unit 37 (Step S303).

Once the second connection unit 210 receives the application name and the personal information, the control unit 203 of the station 20A sends the received application name and personal information to the tablet terminal 10 via the first connection unit 204 (Step S304). Once the connection unit 107 receives the application name and the personal information, the control unit 102 of the tablet terminal 10 initiates the imaging unit 101, and displays a moving image recording screen for moving image recording on the display unit 103 (Step S305). An image taken by the imaging unit 101 is displayed on the moving image recording screen. Besides, the received personal information and application name are also displayed on the moving image recording screen.

Then, the helper SP inputs, to the rehabilitation support apparatus 300, rehabilitation start instruction information that instructs start of rehabilitation (Step S306). Once the manipulation unit 35 acquires the rehabilitation start instruction information, the control unit 34 of the rehabilitation support apparatus 300 executes the specified application to display the target image M1 on the output device 200 and start rehabilitation of the subject EP (Steps S307 to S309). In addition, at the time of rehabilitation start, the transmitting and receiving controller 3410 of the control unit 34 sends start information indicating rehabilitation start to the station 20A via the connection unit 37 (Step S310). Once the second connection unit 210 receives the start information, the control unit 203 of the station 20A sends the received start information to the tablet terminal 10 via the first connection unit 204 (Step S311). Once the connection unit 107 receives the start information, the control unit 102 of the tablet terminal 10 starts recording a moving image taken by the imaging unit 101 (Step S312).

The sensor 100 keeps detecting the action of the subject EP and outputting it to the rehabilitation support apparatus 300 (Steps S313 and S314). In the rehabilitation support apparatus 300, the input unit 31 acquires detection result information and outputs the detection result information to the control unit 34. In the control unit 34, once acquiring the detection result information, the recognition unit 341 selects detection target portion data from the acquired detection result information (Step S315). For example, the recognition unit 341 selects positional information of hands (e.g. the back of his/her hands) from the detection result information. The recognition unit 341 outputs the detection target portion and its positional information thus selected to the recording unit 344. The recording unit 344 records detection result information of the detection target portion in the detection history information storage 333 (Step S316).

Then, once the rehabilitation is over, the rehabilitation support apparatus 300 ends the processing of generating and outputting the target image M1 and the processing of detecting the detection target portion and recording its data which are executed by the control unit 34. For example, once the helper SP inputs rehabilitation end instruction information (Step S317), the control unit 34 acquires this information via the manipulation unit 35 and judges the end of rehabilitation (Step S318). Besides, the control unit 34 also judges the end of rehabilitation when the subject EP goes out of the detection range 800 or the hand of the subject EP goes out of the detection range 800, or when the rehabilitation execution period previously set elapses.

In addition, once the rehabilitation is over, the transmitting and receiving controller 3410 of the control unit 34 sends stop information indicating rehabilitation end to the station 20A via the connection unit 37 (Step S319). Once the second connection unit 210 receives the stop information, the control unit 203 of the station 20A sends the received stop information to the tablet terminal 10 via the first connection unit 204 (Step S320). Once the connection unit 107 receives the stop information, the control unit 102 of the tablet terminal 10 stops recording of a moving image taken by the imaging unit 101 (Step S321), and writes and saves moving image data in the storage unit 104 (Step S322). At this time, the control unit 102 stores the moving image in association with the patient number included in the personal information and the application name, which are received from the station 20A, and the time and date when the moving image recording ends (the time and date when the image is taken). Specifically, the control unit 102 writes the patient number, the application name, the time and date when the image is taken, and the moving image in the correspondence table stored in the storage unit 104 while associating them with each other. In other words, the subject, the application name, and the time and date when the image is taken are associated with the moving image automatically. To put it another way, by simply inputting the personal information of the subject and the application to be executed into the rehabilitation support apparatus 300, these sets of information are automatically input into the tablet terminal 10 and associated with the moving image. Thereby, it is possible to save the helper SP the trouble of entering these sets of information into the tablet terminal 10, and thus improve operability. This makes it possible to reduce the operational burden of the helper SP.

Further, the display controller 342 of the rehabilitation support apparatus 300 generates, from detection target portion data (detection target information) of the subject EP recorded in the detection history information storage 333, a resultant image for displaying an action result of the subject EP in this rehabilitation (e.g. the trajectory of an action of the detection target portion) (Step S323), and displays the resultant image on the output device 200. The transmitting and receiving controller 3410 also sends the resultant image generated by the display controller 342 to the station 20A via the connection unit 37 (Step S324). Once the second connection unit 210 receives the resultant image, the control unit 203 of the station 20A sends the received resultant image to the tablet terminal 10 via the first connection unit 204 (Step S325). Once the connection unit 107 receives the resultant image, the control unit 102 of the tablet terminal 10 writes and saves this resultant image into the storage unit 104 while associating it with the moving image (Step S326). Specifically, the control unit 102 writes image data of the resultant image into the storage unit 104 and, at the same time, writes an image data name of the resultant image into the correspondence table stored in the storage unit 104 while associating it with the moving image. Thereby, the moving image and the resultant image can be stored in association with each other.

Furthermore, the recorded moving image can be reproduced then and there. For example, the helper SP can detach the tablet terminal 10 from the station 20A and check the recorded moving image with the subject EP. Since the tablet terminal 10 is detachable from the station 20A, the subject EP does not need to go to the location where the station 20A is placed. Because the location of the subject EP is the point of taking an image, it is often located away from the station 20A. In this case, the helper can detach the tablet terminal 10 from the station 20A and bring it to the place of the subject EP. Thereby, the helper SP and the subject EP can check and share the recorded moving image at the location where the image is taken.

Once the moving image recording is over, the display controller 1022 of the control unit 102 of the tablet terminal displays, on the display unit 103, a moving image reproduction screen for reproducing the recorded moving image (Step S327).

Note that, in the processing described above, the rehabilitation support apparatus 300 and the tablet terminal 10 may communicate with each other without via the station 20A. In other words, the function of the station 2 OA may be partially or wholly implemented by the applications of the tablet terminal 10.

Figure 21:
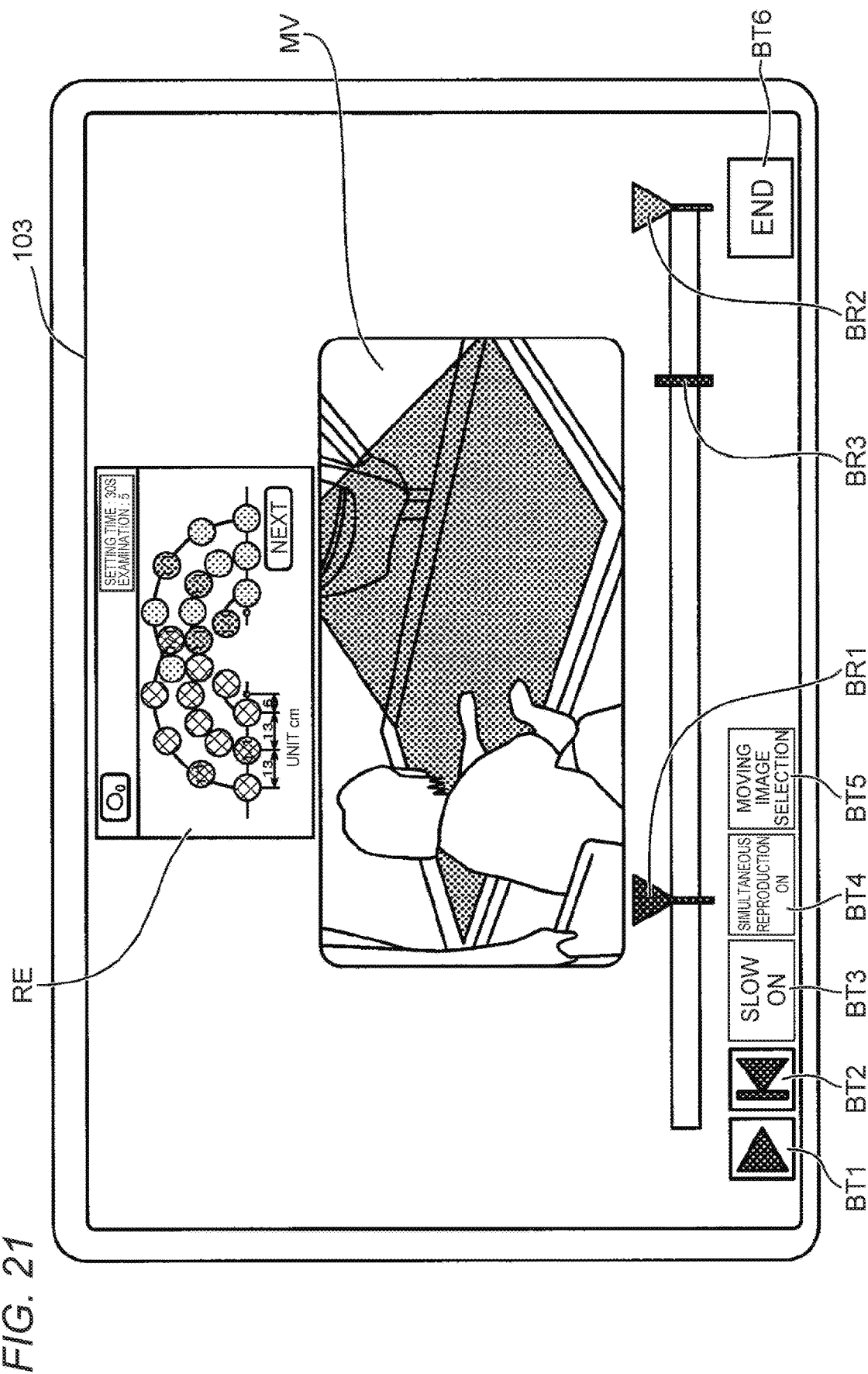
FIG. 21 is a conceptual view illustrating an example of a moving image reproduction screen displayed on a display unit of the tablet terminal in the second embodiment of the present invention.

FIG. 21 is a conceptual view illustrating an example of the moving image reproduction screen displayed on the display unit 103 of the tablet terminal 10. In the moving image reproduction screen illustrated in this drawing, a resultant image area RE for displaying a resultant image, a reproduction area MV for reproducing a moving image, the reproduction button BT1 for reproducing a moving image, the reset button BT2 for resetting the current reproduction position to a reproduction start position, the slow ON button BT3 for reproducing a moving image at a slow rate, the simultaneous reproduction ON button BT4 for reproducing multiple moving images at the same time, the moving image selection button BT5 for selecting a moving image to be reproduced, and the end button BT6 for ending the moving image reproduction screen and moving back to the original screen are arranged. The functions of the buttons BT1 to BT6 are the same as those of the first embodiment.

Further, in the moving image reproduction screen, the reproduction location bar BR1, the end location bar BR2, and the current position bar BR3 are arranged below the reproduction area MV. The functions of the bars BR1 to BR3 are the same as those of the first embodiment.

In the moving image reproduction screen, a moving image can be reproduced with a resultant image corresponding to the moving image displayed thereon. Thus, it is possible to examine the rehabilitation result while comparing it with the moving image, which further facilitates checking.

Further, the tablet terminal 10 can reproduce a moving image taken in the past and a moving image taken this time at the same time in order to compare the current action (the rehabilitation behavior) with the past action. The helper SP presses the simultaneous reproduction ON button BT4. Once the simultaneous reproduction ON button BT4 is pressed in the moving image reproduction screen and its input is accepted, the display controller 1022 of the control unit 102 of the tablet terminal 10 displays, on the display unit 103, the moving image selection screen for selecting the past moving image to be reproduced at the same time.

Figure 22:
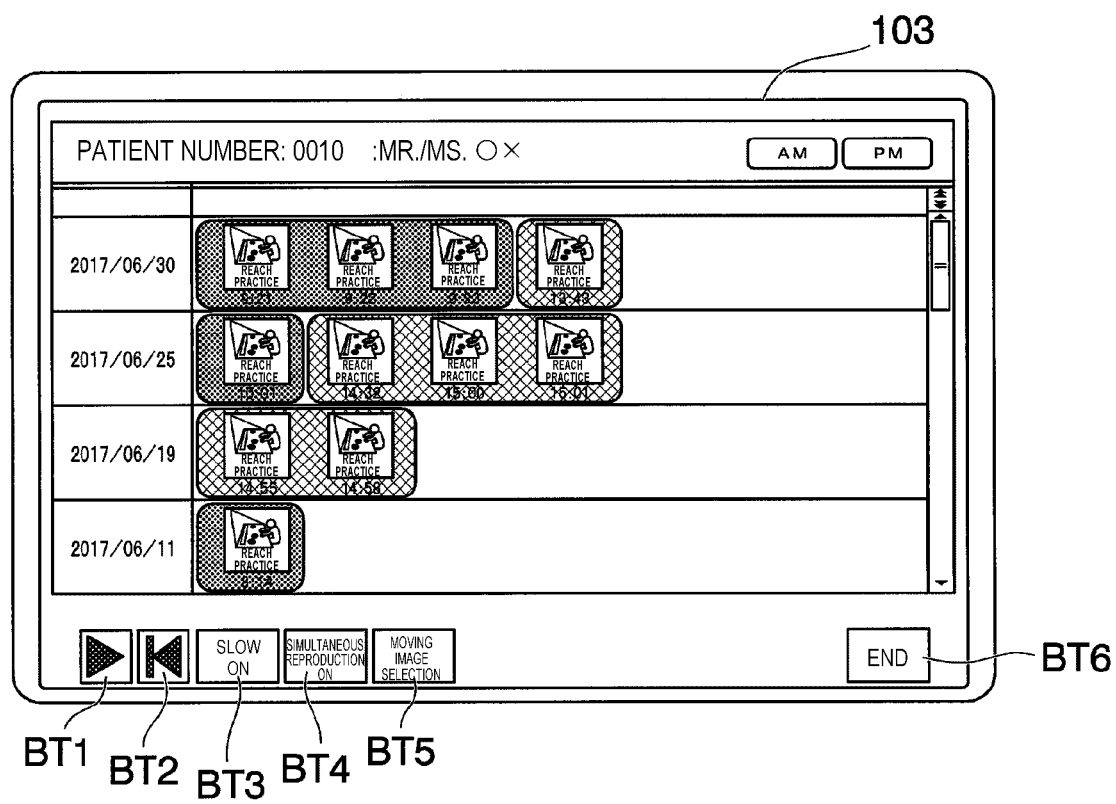
FIG. 22 is a conceptual view illustrating an example of a moving image selection screen displayed on the display unit of the tablet terminal in the second embodiment of the present invention.

FIG. 22 is a conceptual view illustrating an example of the moving image selection screen displayed on the display unit 103 of the tablet terminal 10. In the moving image selection screen illustrated in this drawing, the patient number and name of the subject EP are displayed in its upper left portion, and icons indicating moving images of the subject EP are selectively listed. Each icon is constituted of a pictogram and a text indicating the application executed by the subject EP in the corresponding moving image. Thereby, the application executed by the subject EP in each moving image can be identified easily. By representing the application with a pictogram, it is possible to transmit the content of the application intuitively without language constraint, thus implementing representation suitable for globalization.

As illustrated in the drawing, the icons are displayed while being sorted by date when the moving images are taken. In addition, the time when the image is taken is displayed below each icon. Further, each icon is displayed in such a manner that whether the time when the image is taken in the corresponding date is in the morning or in the afternoon is easily identifiable. For example, the icons can be separated by color in such a way that icons in the morning are circled with a red area while icons in the afternoon are circled with a blue area.

Note that, only moving images belonging to the application of the moving image reproduced in the moving image reproduction screen (i.e. the application executed by the rehabilitation support apparatus 300) may be listed in the moving image selection screen. Alternatively, the icons may be displayed in the moving image selection screen while being sorted by applications.

In the moving image selection screen, the helper SP selects and presses the icon of the moving image to be reproduced at the same time. The display controller 1022 of the control unit 102 of the tablet terminal 10 reads, from the storage unit 104, the moving image of the icon selected in the moving image selection screen and the resultant image corresponding to this moving image, and displays a simultaneous reproduction screen on the display unit 103.

Figure 23:
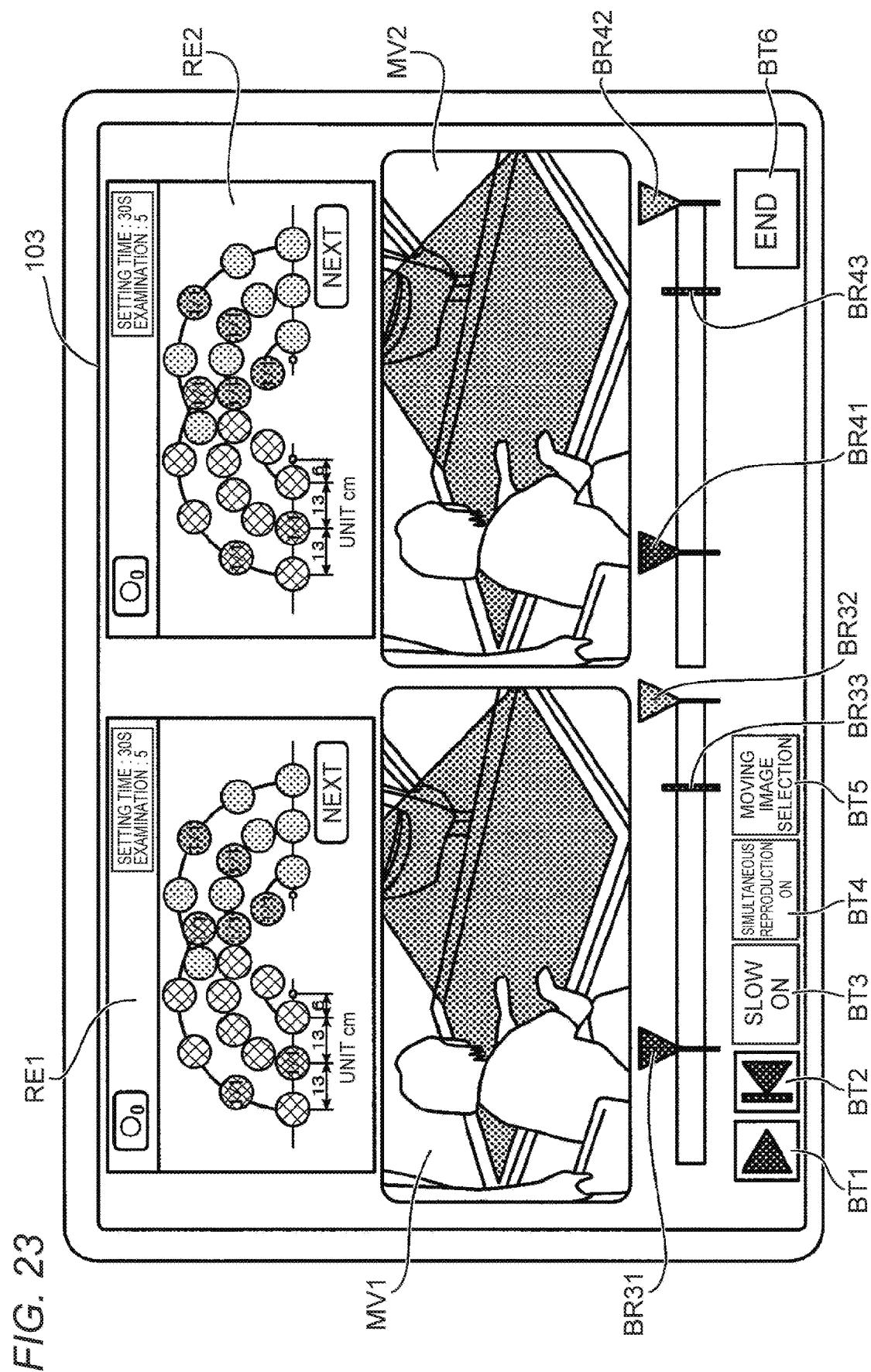
FIG. 23 is a conceptual view illustrating an example of a simultaneous reproduction screen displayed on the display unit of the tablet terminal in the second embodiment of the present invention.

FIG. 23 is a conceptual view illustrating an example of the simultaneous reproduction screen displayed on the display unit 103 of the tablet terminal 10. In the simultaneous reproduction screen illustrated in this drawing, a resultant image area RE1 for displaying a resultant image corresponding to a moving image taken this time, this time's reproduction area MV1 for reproducing a moving image taken this time, a resultant image area RE2 for displaying a resultant image corresponding to a moving image taken in the past, a past reproduction area MV2 for reproducing a moving image taken in the past, and the buttons BT1 to BT6 are arranged. This time's moving image is a moving image reproduced in the moving image reproduction screen, and is a moving image taken most recently, for example. In addition, the past moving image is a moving image selected in the moving image selection screen. Further, the functions of the buttons BT1 to BT6 in the simultaneous reproduction screen are the same as those in the moving image reproduction screen.

Once the reproduction button BT1 is pressed in the simultaneous reproduction screen and its input is accepted, the display controller 1022 of the control unit 102 reproduces this time's moving image in the reproduction area MV1 and the past moving image in the reproduction area MV2 at the same time. In other words, the tablet terminal 10 can reproduce this time's moving image and the past moving image side by side at the same time. Since the tablet terminal can reproduce the two moving images side by side at the same time in one screen, it is possible to easily compare the current moving image with the past moving image at the location where the image is taken. Accordingly, the subject EP can easily check on site how much his/her condition has been recovered (rehabilitation effect) as compared with the past (e.g. when the subject entered the hospital). Thereby, the helper SP and the subject EP can compare the moving images and share the problem at the location where the image is taken, and execute a rehabilitation menu to deal with the problem.

In the meantime, in the simultaneous reproduction screen, a reproduction location bar BR31, an end location bar BR32, and a current position bar BR33 corresponding to this time's moving image are arranged below this time's reproduction area MV1. In addition, in the simultaneous reproduction screen, a reproduction location bar BR41, an end location bar BR42, and a current position bar BR43 corresponding to the past moving image are arranged below the past reproduction area MV2. The functions of the bars BR31 to BR33 are the same as the functions of the bars BR11 to BR13 in the first embodiment, and the functions of the bars BR41 to BR43 are the same as the functions of the bars BR21 to BR23 in the first embodiment. The reproduction location bars BR1, BR31, and BR41 and the end location bars BR2, BR32, and BR42 constitute a reproduction position specification unit configured to specify a reproduction position of a moving image. The display controller 1022 reproduces a moving image at a reproduction position specified by the reproduction position specification unit.

In addition, as in the first embodiment, the tablet terminal 10 includes functions such as: the function of reproducing any desired moving image (including the function of reproducing any desired two moving images at the same time); and the data migration function of transferring a moving image to another equipment (including the automatic data migration function).

Figure 24:
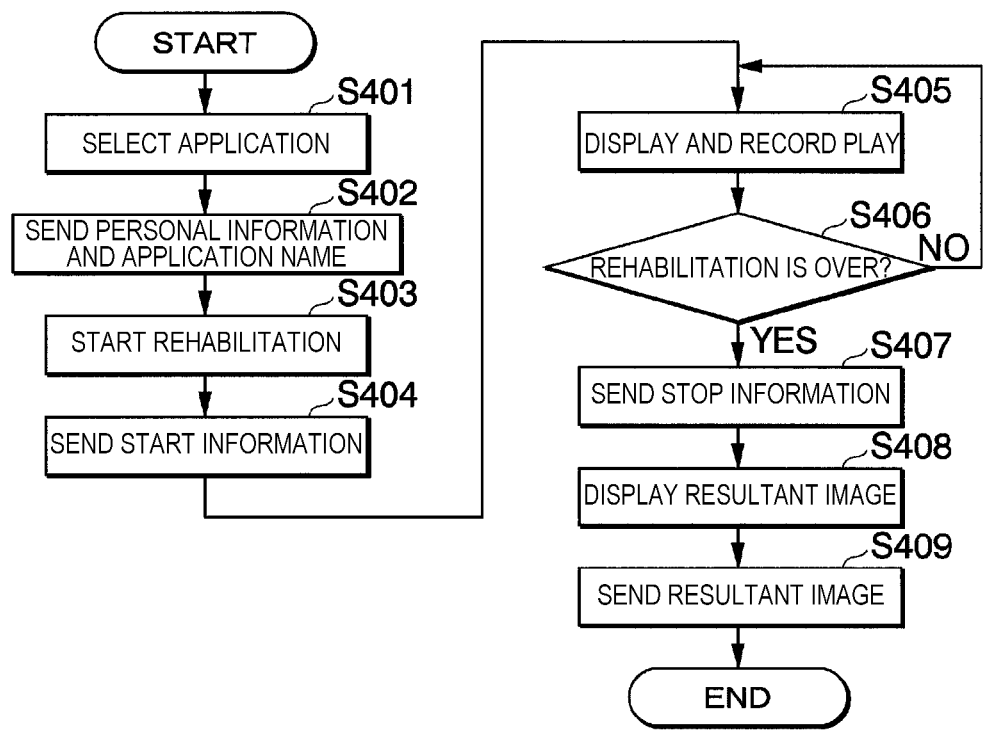
FIG. 24 is a flowchart illustrating an example of application execution processing executed by a rehabilitation support apparatus in the second embodiment of the present invention.

FIG. 24 is a flowchart illustrating an example of application execution processing executed by the rehabilitation support apparatus 300. This drawing illustrates processing of the rehabilitation support apparatus 300 executing an application related to rehabilitation. The helper SP inputs the personal information of the subject EP into the rehabilitation support apparatus 300 and selects an application to be executed.

(Step S401) The control unit 34 accepts an input of application selection at the manipulation unit 35. Then, the process moves to processing in Step S402.

(Step S402) The control unit 34 sends the input personal information and the application name of the selected application to the station 20A via the connection unit 37. Then, the process moves to processing in Step S403.

(Step S403) The control unit 34 executes the selected application and starts playing the rehabilitation of the subject EP. Then, the process moves to processing in Step S404.

(Step S404) The control unit 34 sends start information to the station 20A via the connection unit 37. Then, the process moves to processing in Step S405.

(Step S405) The control unit 34 displays and records the play. Specifically, the control unit 34 displays a target image on the output unit 200 and, at the same time, causes the sensor 100 to detect the detection target portion of the subject EP and records the detection result information thus detected. Then, the process moves to processing in Step S406.

(Step S406) The control unit 34 judges whether or not the rehabilitation play is over. If the control unit 34 judges that the rehabilitation play is over, the process moves to Step S407. On the other hand, if the control unit 34 judges that the rehabilitation play is not over, the process moves back to the processing in Step S405.

(Step S407) The control unit 34 sends stop information to the station 20A via the connection unit 37. Then, the process moves to processing in Step S408.

(Step S408) The control unit 34 generates a resultant image, and displays the generated resultant image on the output device 200. Then, the process moves to processing in Step S409.

(Step S409) The control unit 34 sends the generated resultant image to the station 20A via the connection unit 37. Then, the processing terminates.

Figure 25:
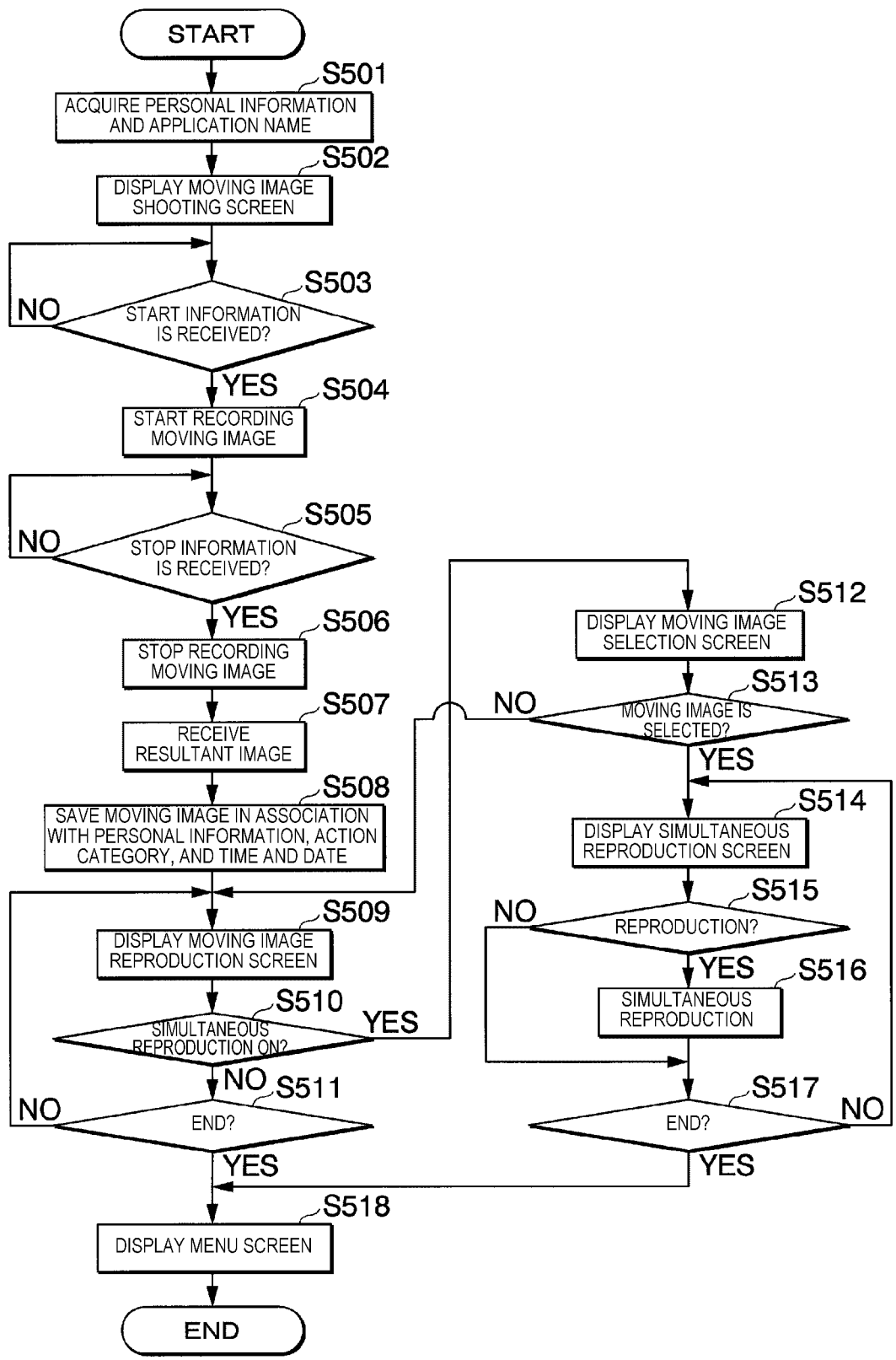
FIG. 25 is a flowchart illustrating an example of moving image record reproduction processing executed by the tablet terminal in the second embodiment of the present invention.

FIG. 25 is a flowchart illustrating an example of moving image record reproduction processing executed by the tablet terminal 10. This drawing illustrates processing of the tablet terminal 10 taking and recording a moving image of the subject EP and reproducing the recorded moving image.

The tablet terminal 10 executes the processing illustrated in this drawing upon receipt of personal information and an application name from the station 20A.

Upon receipt of the personal information and the application name from the rehabilitation support apparatus 300 in Step S402 above, the station 20A outputs the personal information and the application name thus received to the tablet terminal 10.

(Step S501) The control unit 102 acquires the personal information and the application name received from the station 20A via the connection unit 107. Then, the process moves to processing in Step S502.

(Step S502) The control unit 102 initiates the imaging unit 101, and displays a moving image shooting screen on the display unit 103. Then, the process moves to processing in Step S503.

(Step S503) The control unit 102 judges whether or not the connection unit 107 has received, via the station 20A, the start information sent by the rehabilitation support apparatus 300 in Step S404 above. If the control unit 102 judges that the connection unit has received the start information, the process moves to processing in Step S504. On the other hand, if the control unit 102 judges that the connection unit has not received the start information, the process executes the processing in Step S503 again.

(Step S504) The control unit 102 starts recording the moving image taken by the imaging unit 101. Then, the process moves to processing in Step S505.

(Step S505) The control unit 102 judges whether or not the connection unit 107 has received, via the station 20A, the stop information sent by the rehabilitation support apparatus 300 in Step S407 above. If the control unit 102 judges that the connection unit has received the stop information, the process moves to processing in Step S506. On the other hand, if the control unit 102 judges that the connection unit has not received the stop information, the process executes the processing in Step S505 again.

(Step S506) The control unit 102 stops recording the moving image. Then the process moves to processing in Step S507.

(Step S507) The connection unit 107 receives, via the station 20A, the resultant image sent by the rehabilitation support apparatus 300 in Step S409 above. Then, the process moves to processing in Step S508.

(Step S508) The control unit 102 writes and saves the recorded moving image in the storage unit 104 in association with the personal information and the application name acquired in Step S501, the time and date when the recording ends, and the resultant image received in Step S507. Then, the process moves to processing in Step S509.

(Step S509) The control unit 102 displays, on the display unit 103, a moving image reproduction screen for reproducing the recorded moving image. Then, the process moves to processing in Step S510.

(Step S510) The control unit 102 judges whether or not the simultaneous reproduction ON button is pressed in the moving image reproduction screen and its input is accepted. If the control unit 102 judges that its input is accepted, the process moves to processing in Step S412. On the other hand, if the control unit 102 judges that its input is not accepted, the process moves to processing in Step S511.

(Step S511) The control unit 102 judges whether or not the end button is pressed in the moving image reproduction screen and its input is accepted. If the control unit 102 judges that its input is accepted, the process moves to processing in Step S518. On the other hand, if the control unit 102 judges that its input is not accepted, the process moves back to the processing in Step S509.

(Step S512) The control unit 102 displays a moving image selection screen on the display unit 103. Then, the process moves to processing in Step S513.

(Step S513) The control unit 102 judges whether or not a moving image to be simultaneously reproduced is selected in the moving image selection screen. If the control unit 102 judges that the moving image to be simultaneously reproduced is selected, the process moves to processing in Step S514. On the other hand, if the control unit 102 judges that no moving image to be simultaneously reproduced is selected, the process moves back to the processing in Step S509.

(Step S514) The control unit 102 displays, on the display unit 103, a simultaneous reproduction screen for reproducing the moving image selected in the moving image selection screen and the recorded moving image at the same time. Then, the process moves to processing in Step S515.

(Step S515) The control unit 102 judges whether or not the reproduction button is pressed in the simultaneous reproduction screen and its input is accepted. If the control unit 102 judges that its input is accepted, the process moves to processing in Step S516. On the other hand, if the control unit 102 judges that its input is not accepted, the process moves to processing in Step S517.

(Step S516) The control unit 102 reproduces the selected moving image and the recorded moving image at the same time. Then, the process moves to processing in Step S517.

(Step S517) The control unit 102 judges whether or not the end button is pressed in the simultaneous reproduction screen and its input is accepted. If the control unit 102 judges that its input is accepted, the process moves to processing in Step S518. On the other hand, if the control unit 102 judges that its input is not accepted, the process moves back to the processing in Step S514.

(Step S518) the control unit 102 displays a menu screen on the display unit 103 and executes each processing specified. Then, the processing terminates.

As has been described above, the rehabilitation support system S2 of this embodiment includes: the portable tablet terminal 10; and the station 20A to and from which the tablet terminal 10 is attachable and detachable. The station 20A includes: the second connection unit 210 configured to receive and acquire subject identification information for identifying the rehabilitation subject from the rehabilitation support apparatus 300 that executes an application related to rehabilitation performed by the subject; the first connection unit 204 configured to be connected to the tablet terminal 10 and transmit and receive data to and from the tablet terminal when the tablet terminal 10 is attached to the station; and the control unit 203 configured to send the subject identification information, acquired by the second connection unit 210, to the tablet terminal 10 via the first connection unit 204. The tablet terminal 10 includes: the connection unit 107 configured to be connected to the station 20A and transmit and receive data to and from the station when the tablet terminal is attached to the station; the imaging unit 101 configured to take an image of the subject; the storage unit 104 configured to store a moving image taken by the imaging unit 101; and the recording controller 1021 configured to receive the subject identification information from the station 20A via the connection unit 107 and write the moving image of the subject, taken by the imaging unit 101, in the storage unit 104 while associating it with the received subject identification information.

According to the above configuration, the subject identification information that the station 20A has received from the rehabilitation support apparatus 300 is automatically associated with the moving image and stored in the tablet terminal 10. This enables the taken moving image to be stored on a per-subject basis by simply inputting the subject identification information in the rehabilitation support apparatus 300. Accordingly, the helper SP does not need to check moving images and sort them by subjects after his/her work is over, thereby improving operability.

In addition, in the rehabilitation support system S2 of this embodiment, the second connection unit 210 acquires a rehabilitation-related action category (application name) together with subject identification information, the control unit 203 sends the action category together with the subject identification information to the tablet terminal 10 via the first connection unit 204, and the recording controller 1021 writes a moving image in the storage unit 104 while associating it with the subject identification information and action category thus received.

According to the above configuration, the application executed by the rehabilitation support apparatus 300 is automatically associated with the moving image and stored in the tablet terminal 10. This makes it possible to store, by simple manipulation, moving images of the subject while sorting them by subjects and action categories. Thereby, the helper SP does not need to check moving images and sort them by action categories after his/her work is over, thus improving operability.

Further, in the rehabilitation support system S2 of this embodiment, the tablet terminal 10 includes the display unit 103 configured to reproduce and display a moving image stored in the storage unit 104, and the display controller 1022 configured to reproduce multiple moving images of the subject at the same time while displaying them on the display unit 103 side by side. According to the above configuration, it is possible to reproduce multiple moving images stored in the tablet terminal 10 at the same time while displaying them side by side. Hence, by reproducing a moving image of the past rehabilitation behavior and a moving image of the current rehabilitation behavior at the same time and comparing them with each other, for example, it is possible to compare the current rehabilitation behavior with the past one easily. Thereby, it is possible to present the subject with a rehabilitation effect, a recovery state, and the like more intuitively.

Furthermore, in the rehabilitation support system. S2 of this embodiment, the tablet terminal 10 includes the reproduction position specification unit (the reproduction location bars BR31, BR41, and BR51 and the end location bars BR32, BR42, and BR52) which specify a reproduction position of the moving image, and the display controller 1022 reproduces a moving image at a reproduction position specified by the reproduction position specification unit. According to the above configuration, it is possible to adjust the reproduction position of each of moving images to be reproduced at the same time. Accordingly, it is possible to reproduce multiple moving images at the same time while adjusting the reproduction position of each moving image to its action start timing, for example, and thus compare the multiple moving images more easily.

Hereinabove, the embodiments of this invention have been described in detail with reference to the drawings; however, its specific configuration is not limited to those of these embodiments, and includes designs and the like within a range not departing from the gist of this invention.

For example, in the above embodiments, the subject, the action category, and the time and date are associated with the moving image by way of the correspondence table; however, not limited thereto, the system may have such a configuration that the subject, the action category, and the time and date are associated with the moving image by other methods such as a method of generating folders corresponding to the respective action categories for every subject and sorting sets of moving image data added with the time and date into the folders.

Meanwhile, in the above embodiments, two moving images are reproduced at the same time in the simultaneous reproduction screen; however, two or more moving images may be reproduced at the same time.

Meanwhile, the above embodiment have been described with the example in which the system includes one tablet terminal 10 and one station 20 or 20A; however, not limited thereto, the system may have such a configuration as to include multiple tablet terminals 10 and multiple stations 20 or 20A. In addition, the number of tablet terminals 10 may be different from the number of stations 20 or 20A. For example, the number of stations 20 or 20A may be larger than the number of tablet terminals 10. By arranging multiple stations 20 or 20A at different locations, it is possible to take images at various positions. In the case where there are multiple tablet terminals 10, the system may have such a configuration that, for example, a server or the like for managing synchronization between the terminals is installed and the server or the like synchronizes data by periodically extracting difference data from the latest updated data from each of the tablet terminals 10, or alternatively the server or the like manages information of all the tablet terminals 10 and performs comparison between moving images and various outputs described above in an integrated fashion.

Meanwhile, in the above embodiments, the tablet terminal 10 takes an image while being placed at the station 20 or 20A; however, not limited thereto, the system may have such a configuration that the helper or the subject detaches the tablet terminal 10 from the station 20 or 20A and takes an image after inputting the patient number and the action category. Thereby, it is possible to take an image at any desired location. For example, the helper SP or the subject EP can take an image while holding the tablet terminal 10 by hands directly.

Meanwhile, by taking a screenshot at a timing of characteristic actions in the moving image reproduction screen or the simultaneous reproduction screen, it is possible to acquire a still image of that scene. By printing and outputting a group of still images acquired by screenshot and still images acquired by automatic OUTPUT and manual OUTPUT, it is possible to keep their records in a nursing report and a patient daily report, for example.

Meanwhile, it is also possible to share moving images, taken by the tablet terminal 10, together with electronic medical records. Thereby, all of those engaged in medical service can share and know the condition of each subject EP.

Meanwhile, the tablet terminal 10 may calculate the joint angle, the movement trajectory, the amount of movement, and the like from a moving image by use of an application additionally installed. This enables further technical data extraction from a moving image. Additionally, the system may have such a configuration as to put stickers for analysis or the like on the body (e.g. joints) of the subject EP, and calculate the movement trajectory, the amount of movement, and the like of each sticker or the like in a moving image.

In this case, it is possible to further improve accuracy in the analysis of the movement trajectory, the amount of movement, and the like.

Meanwhile, the tablet terminal 10 can register data on the subject EP, measured by another equipment, by using the unified patient number with this equipment. Note that various methods are conceivable as a data share method and a communication method.

Meanwhile, the station 20 can be moved easily by providing a portable stand to the station 20. Thereby, it is possible to take images of various scenes such as a scene of mealtime at a hospital ward and actions at the hospital ward. More specifically, it is possible to take images of an occupational therapy, images of speech practice taken by a speech therapist, images of a swallowing behavior at mealtime taken by a speech therapist, and images taken by a nurse for checking the safety of actions at or near a bed, for example.

Meanwhile, the tablet terminal 10 may work with a web camera to take images of the subject EP at two or more separate locations at the same time. In the case of recording actions during rehabilitation, it is necessary to take images at two locations such as ahead of and beside the subject. Thus, the tablet terminal 10 may be connected to a web camera to take images of the subject EP at multiple locations at the same time. Note that, a web camera can take images by itself, which facilitates taking images at a different place.

Meanwhile, in the above embodiments, the description has been made of the case of taking images of actions related to rehabilitation; however, the field of taking moving images is not limited to this. The action categories to be associated with the pairing reader 201 of the station 20 are customizable, and hence the system can be used in various fields such as a care field and a nursing-care field. In addition, the number of read areas (i.e. action categories) of the pairing reader 201 is not limited to five, and may be less than five or larger than five. For example, the action categories may be changed by changing a board set in the pairing reader 201. In each board, the action categories corresponding to the respective read areas are set. The system may have such a configuration as to previously prepare boards in which the action categories are previously set, or alternatively as to be capable of making settings of the action categories freely.

Meanwhile, in the case of taking an image of walking, for example, a wide-range image is often needed. Thus, a fish-eye lens may be set in the imaging unit 101. By taking a wide-range image, it is possible to take a moving image effectively in a small room.

Note that, the system may have such a configuration as to perform the kinds of processing, performed by the tablet terminal 10, the stations 20 and 20A, and the rehabilitation support apparatus 300 described above, by: recording a program for implementing the functions of the tablet terminal 10, the stations 20 and 20A, and the rehabilitation support apparatus 300 described above into a computer-readable recording medium; loading the program recorded in this recording medium in a computer system; and executing the program. Here, "loading the program recorded in this recording medium in a computer system; and executing the program" includes installing the program in the computer system. The "computer system" mentioned here shall include hardware such as an OS and peripheral devices. In addition, the "computer system" may include multiple computer devices which are connected to each other via a network including a communication line such as the internet, WAS, LAN and a dedicated line. Further, the "computer readable recording medium" indicates a portable medium such as a flexible disk, a magnetooptical disk, a ROM, and a CD-ROM, or a storage device such as a hard disk built into the computer system. In this way, the recording medium storing the program therein may be a non-transient recording medium such as a CD-ROM.

In addition, the recording medium includes a recording medium that is provided inside or outside a distribution server and accessible to the distribution server for distributing the program. A program code stored in the recording medium of the distribution server may be different from a program code executable in a terminal device. In other words, the program may be stored in the distribution server in any format as long as it can be downloaded from the distribution server and installed in the terminal device in an executable format. Note that the system may have such a configuration as to divide the program into multiple parts, download these parts at different timings, and then synthesize them in the terminal device, and as to have different distribution servers for distributing the divided program respectively. Further, the "computer-readable recording medium" shall include a medium that holds a program for a given period of time, such as a volatile memory (RAM) inside a computer system serving as a server or client in the case of transmitting a program via a network. Alternatively, the above program may be a program for implementing a part of the functions described above. Still alternatively, the program may be a difference file (difference program) i.e. one implemented by using the above functions in combination with a program previously recorded in a computer system.

Additional Note 1

(1) A moving image recording method in a moving image recording system including an information processor and a station to and from which the information processor is attachable and detachable, the method including the steps of: causing the station to be connected to the information processor and transmit and receive data to and from the information processor; causing the station to acquire subject identification information for identifying a subject of an image; causing the station to send the acquired subject identification information to the information processor; causing the information processor to be connected to the station and transmit and receive data to and from the station; causing the information processor to take an image of the subject; causing the information processor to store a moving image thus taken; and causing the information processor to receive the subject identification information from the station, and write the taken moving image of the subject into the storage unit while associating the moving image with the subject identification information thus received.

(2) A program in a moving image recording system including an information processor and a station to and from which the information processor is attachable and detachable, the program causing a computer of the station to execute the processes of: being connected to the information processor and transmitting and receiving data to and from the information processor; acquiring subject identification information for identifying a subject of an image; and sending the acquired subject identification information to the information processor, the program causing a computer of the information processor to execute the processes of: being connected to the station and transmitting and receiving data to and from the station; taking an image of the subject; storing a moving image thus taken; and receiving the subject identification information from the station, and writing the taken moving image of the subject into a storage unit while associating the moving image with the subject identification information thus received.

(3) A station in a moving image recording system including an information processor and the station to and from which the information processor is attachable and detachable, the station including: a connection unit configured to be connected to the information processor and transmit and receive data to and from the information processor; an acquisition unit configured to acquire subject identification information for identifying a subject of an image; and a control unit configured to send the subject identification information, acquired by the acquisition unit, to the information processor via the connection unit.

(4) A moving image recording method to be executed by a station in a moving image recording system including an information processor and the station to and from which the information processor is attachable and detachable, the method including the steps of: acquiring subject identification information for identifying a subject of an image; and sending the acquired subject identification information to the information processor via a connection unit configured to be connected to the information processor and transmit and receive data to and from the information processor.

(5) A program in a moving image recording system including an information processor and a station to and from which the information processor is attachable and detachable, the program causing a computer of the station to execute the processes of: acquiring subject identification information for identifying a subject of an image; and sending the acquired subject identification information to the information processor via a connection unit configured to be connected to the information processor and transmit and receive data to and from the information processor.

(6) An information processor in a moving image recording system including the information processor and a station to and from which the information processor is attachable and detachable, the information processor including: a connection unit configured to be connected to the station and transmit and receive data to and from the station; an imaging unit configured to take an image of the subject; a storage unit configured to store a moving image taken by the imaging unit; and a recording controller configured to receive the subject identification information for identifying a subject from the station via the connection unit, and write the moving image of the subject, taken by the imaging unit, into the storage unit while associating the moving image with the subject identification information thus received.

(7) A moving image recording method to be executed by an information processor in a moving image recording system including the information processor and a station to and from which the information processor is attachable and detachable, the method including the steps of: receiving subject identification information for identifying a subject from the station via a connection unit configured to be connected to the station and transmit and receive data to and from the station; taking an image of the subject; and writing the taken moving image of the subject into a storage unit while associating the moving image with the subject identification information thus received.

(8) A program in a moving image recording system including an information processor and a station to and from which the information processor is attachable and detachable, the program causing a computer of the information processor to execute the processes of: receiving subject identification information for identifying a subject from the station via a connection unit configured to be connected to the station and transmit and receive data to and from the station; taking an image of the subject; and writing the taken moving image of the subject into a storage unit while associating the moving image with the subject identification information thus received.

[Additional Note 2]

(1) A moving image recording system including an information processor that is attachable to and detachable from a station including: a connection unit configured to transmit and receive data; an acquisition unit configured to acquire subject identification information for identifying a subject of an image; and a control unit configured to send the subject identification information, acquired by the acquisition unit, via the connection unit, in which the information processor includes:

a connection unit configured to be connected to the connection unit of the station and transmit and receive data to and from the station;

an imaging unit configured to take an image of the subject;

a storage unit configured to store a moving image taken by the imaging unit; and a recording controller configured to receive the subject identification information from the station via the connection unit, and write the moving image of the subject, taken by the imaging unit, into the storage unit while associating the moving image with the subject identification information thus received.

(2) The moving image recording system described in the above section (1), in which the information processor includes:

a display unit configured to reproduce and display the moving image stored in the storage unit; and a display controller configured to reproduce the multiple moving images of the subject at the same time while displaying the moving images on the display unit side by side.

(3) The moving image recording system described in the above section (2), in which the information processor includes a reproduction position specification unit configured to specify a reproduction position of the moving image, and the display controller reproduces the moving image in a range corresponding to the reproduction position specified by the reproduction position specification unit.

(4) The moving image recording system described in the above section (3), in which the information processor includes:

the display unit configured to reproduce and display the moving image stored in the storage unit;

the reproduction position specification unit configured to specify a reproduction position of the moving image; and a display controller configured to extract and output a predetermined number of still images from the moving image in the range corresponding to the reproduction position specified by the reproduction position specification unit.

(5) The moving image recording system described in the above section (1), in which the information processor includes:

a display unit configured to reproduce and display the moving image stored in the storage unit;

a reproduction position specification unit configured to specify a reproduction position of the moving image; and a display controller configured to extract and output a predetermined number of still images from the moving image in a range corresponding to the reproduction position specified by the reproduction position specification unit.

(6) The moving image recording system described in the above section (1), in which the information processor includes:

a display unit configured to reproduce and display the moving image stored in the storage unit;

a reproduction position specification unit configured to specify a reproduction position of the moving image; and a display controller configured to extract and output a predetermined number of still images from the moving image in a range corresponding to the reproduction position specified by the reproduction position specification unit.

(7) The moving image recording system described in the above section (1), in which the information processor includes:

a display unit configured to reproduce and display the moving image stored in the storage unit; and a display controller configured to display the moving image of the subject and a resultant image, which corresponds to the moving image and indicates an action result of the subject, on the display unit side by side.

(8) The moving image recording system described in the above section (7), in which the display controller displays the multiple moving images and the multiple resultant images of the subject on the display unit side by side.

(9) The moving image recording system described in the above section (8), in which the information processor includes a reproduction position specification unit configured to specify a reproduction position of the moving image, and the display controller reproduces the moving image in a range corresponding to the reproduction position specified by the reproduction position specification unit.

(10) The moving image recording system described in the above section (8), in which the information processor includes a reproduction position specification unit configured to specify a reproduction position of the moving image, and the display controller extracts and outputs a predetermined number of still images from the moving image in a range corresponding to the reproduction position specified by the reproduction position specification unit.

The rehabilitation support system of each embodiment at least uses the tablet terminal 10 and the station 20; however, not limited thereto, the system may have such a configuration as to add the function of the station 20 to the tablet terminal 10 instead of using the station 20, for example. In this case, as illustrated in a modified example of FIGS. 26A and 26B, the tablet terminal 10 may be supported by a movable support base 120 instead of the station 20.

The movable support base 120 includes: multiple casters 121; multiple leg units 122; a pole 123; a support table 124; a tablet terminal holder 125; and a camera holder 126.

The casters 121 are attached to the respective leg units 122 and capable of running on a floor.

The pole 123 stands in a vertical direction while being supported by the leg units 122, and its length in the vertical direction (height) is adjustable. The pole 123 includes: a pipe 123a that stands on the leg units 122; an extension unit 123b that has a lower end part inserted coaxially into the pipe 123a; and an adjustment unit 123c that is configured to fix, or allow a change in, the vertical position and rotational position of the extension unit 123b relative to the pipe 123a. When the adjustment unit 123c is loosened, the extension unit 123b can vertically move and rotate relative to the pipe 123a, which enables the pole to be adjusted to such a position that the height and orientation in the rotational direction of an external camera EC to be described later may be optimal. After the adjustment is over, the height and rotational position of the extension unit 123b, i.e. the height and rotational position of the external camera EC can be fixed by fastening the adjustment unit 123c.

The support table 124 is fixed at an intermediate position in the vertical direction of the pipe 123a, and is capable of accepting the tablet terminal 10 on its upper face.

Figure 26A:
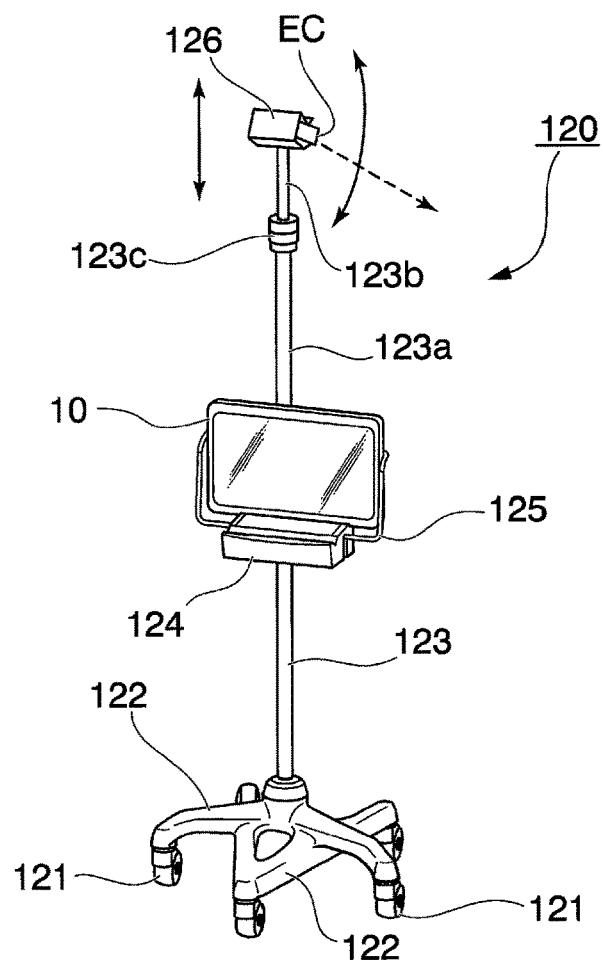
FIG. 26A is a view illustrating a modified example in the first embodiment and the second embodiment of the present invention, and is a perspective view illustrating a mode where the tablet terminal is supported by a movable support mount instead of the station.
Figure 26B:
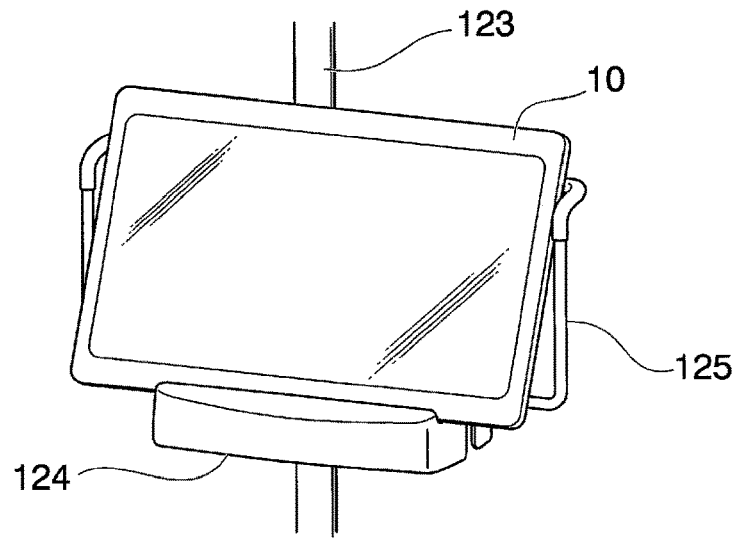
FIG. 26B is a view illustrating this modified example, and is a chief part enlarged view of FIG. 26A.

The tablet terminal holder 125 is designed to hold the tablet terminal 10 in concert with the support table 124. In the case of taking a moving image with the tablet terminal 10 without using the external camera, as illustrated in FIG. 26A, the tablet terminal 10 can be fixed perpendicularly to the upper face of the support table 124. Meanwhile, in the case of manipulating the tablet terminal 10 without taking an image with the tablet terminal, as illustrated in FIG. 26B, its screen becomes easily viewable and its manipulation becomes easier by placing the tablet terminal 10 obliquely on the upper face of the support table 124. In either case, the tablet terminal 10 is supported at its back face by the tablet terminal holder 125.

The camera holder 126 is swingably fixed on the upper end of the extension unit 123b, and the external camera EC (such as a web camera) can be mounted on the camera holder. The camera holder 126 is capable of a lateral oscillating movement and vertical tilting movement. Accordingly, in the case of taking an image with the external camera EC instead of taking an image with the tablet terminal 10, the external camera EC is first fixed on the camera holder 126 so that the external camera may be directed opposite the screen of the tablet terminal 10 (in the direction of the dashed arrow). Then, the height and rotational position of the extension unit 123b are adjusted by manipulating the adjustment unit 123c. Then, the orientation in the up-down direction of the camera holder 126 is adjusted. This enables the external camera EC to be directed at the subject EP when taking an image. In addition, even when the distance between the camera and the subject EP is short, such a situation can be dealt with by changing the orientation of the external camera EC and thus can be dealt with flexibly. For example, even when the rehabilitation place is so small that the distance between the camera and the subject EP is short, it is possible to take an image of the facial expression of the subject EP and the content of his/her work on a table while putting both information on one screen by setting the external camera EC at a high position.

Note that, various kinds of communication including transmission of moving images between the external camera EC and the tablet terminal 10 may be performed by wire or by wireless.

A user can input or select personal information for identifying the subject EP on the screen of the tablet terminal 10. Note that, the name of the subject EP may be registered in the tablet terminal 10 in advance together with the personal information in order for the user to select. Alternatively, the personal information for identifying the subject EP may be registered in the tablet terminal 10 in advance in association with the unique identification number of the subject EP in order for the user to select.

The user can input or select a rehabilitation-related action category on the screen of the tablet terminal 10. For example, action categories such as "sitting position", "standing up", and "walking" are displayed on the tablet terminal 10.

Thereby, the user can use the rehabilitation support system without using the device 40 (without personal setting on the device 40).

In this case, in the sequence of FIG. 7, Step S101 of the device 40 and Step S103 of the station 20 are deleted, and Step S102 of the station 20 is carried out by the tablet terminal 10. In the sequence of FIG. 20, in the steps where signals are input into the station 20A (S303, S310, S319, and S324), the signals are input in the tablet terminal 10. In other words, Steps S303 and S304 are integrated into one step, Steps S310 and S311 are integrated into one step, and Steps S324 and S325 are integrated into one step.

INDUSTRIAL APPLICABILITY

According to this moving image recording system, it is possible to improve its operability.

REFERENCE SIGNS LIST

S1, S2: rehabilitation support system (moving image recording system), 10: tablet terminal (information processor), 20, 20A: station, 30: remote controller, 31: input unit, 32: output unit, 33: storage unit, 34: control unit, 35: manipulation unit, 36: display unit, 37: connection unit, 40, 40-1, 40-2: device, 100: sensor, 101: imaging unit, 102: control unit, 103: display unit, 104: storage unit, 105: manipulation unit, 106: receiver, 107: connection unit, 200: output device, 201: pairing reader (acquisition unit), 202: power feeding unit, 203: control unit, 204: first connection unit (connection unit), 205: docking unit, 210: second connection unit (acquisition unit), 300: rehabilitation support apparatus, 301: manipulation unit, 302: transmitter, 310: leg unit, 311, 312, 313, 314: caster, 331: calibration information storage, 332: judgment condition information storage, 333: detection history information storage, 334: parameter information storage, 335: program information storage, 341: recognition unit, 342: display controller, 343: action area judgment unit, 344: recording unit, 345: target determination unit, 346: evaluation unit, 347: foot display parameter setting unit, 348: hand display parameter setting unit, 349: disturbance display parameter setting unit, 401: storage unit, 1021: recording controller, 1022: display controller, 2011, 2012, 2013, 2014, 2015: read area, 3410: transmitting and receiving controller, BR1, BR11, BR21: reproduction location bar (reproduction position specification unit), BR2, BR12, BR22: end location bar (reproduction position specification unit).

The invention claimed is:

1. A moving image recording system comprising an information processor and a rehabilitation device to and from which the information processor is attachable and detachable, wherein
the rehabilitation device comprises:
a first communication interface configured to communicate with the information processor, the first communication interface being capable of sending a first instruction of starting a rehabilitation activity, and a second instruction of ending a rehabilitation activity;
a detector configured to recognize a portion of a subject while performing a rehabilitation activity, where if an area the subject performs the rehabilitation activity is a floor, the portion is an ankle of the subject and if the area the subject performs the rehabilitation activity is a table, the portion is a hand of the subject;
a projector configured to output a target; and
a first controller configured to evaluate whether a hand or an ankle of the subject can reach the target output by the projector during the rehabilitation activity using a result of recognizing the portion of the subject, and
the information processor comprises:
a second communication interface configured to communicate with the rehabilitation device;
an imaging unit configured to record a moving image of the subject;
a storage unit configured to store a moving image taken by the imaging unit;
a second controller configured to receive the subject identification information from the rehabilitation device via the second communication interface, to start recording the moving image on the basis of the first instruction, to end recording the moving image on the basis of the second instruction, and to write the moving image of the subject, taken by the imaging unit, into the storage unit while associating the moving image with a subject identification information thus received.

2. The moving image recording system according to claim 1, wherein
the information processor further includes an acquisition unit, the acquisition unit acquires an action category together with the subject identification information, and
the second controller of the information processor writes the subject identification information and the action category thus received into the storage unit in association with the moving image.

3. The moving image recording system according to claim 2, wherein the acquisition unit of the information processor reads the subject identification information from a medium storing therein subject identification information.

4. The moving image recording system according to claim 2, wherein the acquisition unit of the information processor includes, for every action category, a selection area for reading and selecting the subject identification information from a medium storing therein subject identification information.

5. The moving image recording system according to claim 2, wherein the acquisition unit of the information processor receives the subject identification information from the rehabilitation device that executes an application related to the rehabilitation activity performed by the subject.

6. The moving image recording system according to claim 1, wherein the acquisition unit of the information processor reads the subject identification information from a medium storing therein subject identification information.

7. The moving image recording system according to claim 1, wherein the acquisition unit of the information processor receives the subject identification information from a rehabilitation support apparatus that executes an application related to the rehabilitation activity performed by the subject.

8. The moving image recording system according to claim 1, wherein the information processor comprises:
a display unit configured to reproduce and display the moving image stored in the storage unit; and
a display controller configured to reproduce a plurality of the moving images of the subject at the same time while displaying the moving images on the display unit side by side.

9. The moving image recording system according to claim 8, wherein
the information processor comprises a reproduction position specification unit configured to specify a reproduction position of the moving image, and the display controller reproduces the moving image in a range corresponding to the reproduction position specified by the reproduction position specification unit.

10. The moving image recording system according to claim 9, wherein the information processor comprises:
   the display unit configured to reproduce and display the moving image stored in the storage unit;
   the reproduction position specification unit configured to specify a reproduction position of the moving image; and
   a display controller configured to extract and output a predetermined number of still images from the moving image in the range corresponding to the reproduction position specified by the reproduction position specification unit.

11. The moving image recording system according to claim 8, wherein the information processor comprises:
   the display unit configured to reproduce and display the moving image stored in the storage unit;
   a reproduction position specification unit configured to specify a reproduction position of the moving image; and
   a display controller configured to extract and output a predetermined number of still images from the moving image in a range corresponding to the reproduction position specified by the reproduction position specification unit.

12. The moving image recording system according to claim 5, wherein the information processor comprises:
   a display unit configured to reproduce and display the moving image stored in the storage unit;
   a reproduction position specification unit configured to specify a reproduction position of the moving image; and
   a display controller configured to extract and output a predetermined number of still images from the moving image in a range corresponding to the reproduction position specified by the reproduction position specification unit.

13. The moving image recording system according to claim 1, wherein the information processor comprises:
   a display unit; and
   a display controller configured to display the moving image of the subject, which is stored in the storage unit, and a resultant image, which corresponds to the moving image and indicates an action result of the subject, on the display unit side by side.

14. The moving image recording system according to claim 13, wherein
   the information processor comprises a reproduction position specification unit configured to specify a reproduction position of the moving image, and
   the display controller reproduces the moving image in a range corresponding to the reproduction position specified by the reproduction position specification unit.

15. The moving image recording system according to claim 13, wherein
   the information processor comprises a reproduction position specification unit configured to specify a reproduction position of the moving image, and
   the display controller extracts and outputs a predetermined number of still images from the moving image in a range corresponding to the reproduction position specified by the reproduction position specification unit.

16. The moving image recording system according to claim 13, wherein the display controller displays a plurality of the moving images and a plurality of the resultant images of the subject on the display unit side by side.

17. The moving image recording system according to claim 16, wherein
   the information processor comprises a reproduction position specification unit configured to specify a reproduction position of each of the moving images, and
   the display controller reproduces the moving image in a range corresponding to the reproduction position specified by the reproduction position specification unit.

18. The moving image recording system according to claim 16, wherein
   the information processor comprises a reproduction position specification unit configured to specify a reproduction position of each of the moving images, and
   the display controller extracts and outputs a predetermined number of still images from the moving image in a range corresponding to the reproduction position specified by the reproduction position specification unit.

* * * * *